(12) United States Patent
Honmou et al.

(10) Patent No.: US 11,666,601 B2
(45) Date of Patent: Jun. 6, 2023

(54) SYNAPSE FORMATION AGENT

(71) Applicants: Sapporo Medical University, Sapporo (JP); Nipro Corporation, Osaka (JP)

(72) Inventors: Osamu Honmou, Hokkaido (JP); Masanori Sasaki, Hokkaido (JP); Rie Maezawa, Hokkaido (JP); Shinichi Oka, Hokkaido (JP); Yuko Sasaki, Hokkaido (JP); Masahito Nakazaki, Hokkaido (JP); Toshihiko Yamashita, Hokkaido (JP)

(73) Assignees: Sapporo Medical University, Hokkaido (JP); Nipro Corporation, Osaka (JP)

( * ) Notice: Subject to any disclaimer, the term of this patent is extended or adjusted under 35 U.S.C. 154(b) by 479 days.

(21) Appl. No.: 16/096,962

(22) PCT Filed: Apr. 26, 2017

(86) PCT No.: PCT/JP2017/017325
§ 371 (c)(1),
(2) Date: Oct. 26, 2018

(87) PCT Pub. No.: WO2017/188457
PCT Pub. Date: Nov. 2, 2017

(65) Prior Publication Data
US 2019/0117700 A1   Apr. 25, 2019

(30) Foreign Application Priority Data

Apr. 28, 2016 (JP) ............................. JP2016-091286
Apr. 28, 2016 (JP) ............................. JP2016-091300

(51) Int. Cl.
*A61K 35/28* (2015.01)
*A61K 9/00* (2006.01)
*A61P 25/00* (2006.01)
*C12N 5/0775* (2010.01)

(52) U.S. Cl.
CPC ............ *A61K 35/28* (2013.01); *A61K 9/0019* (2013.01); *A61P 25/00* (2018.01); *C12N 5/0663* (2013.01)

(58) Field of Classification Search
CPC ........ A61K 35/28; A61K 9/0019; A61P 25/00
See application file for complete search history.

(56) References Cited

U.S. PATENT DOCUMENTS

| 2004/0121461 A1 | 6/2004 | Honmou et al. |
| 2010/0074875 A1 | 3/2010 | Oh et al. |
| 2010/0254953 A1 | 10/2010 | Honmou et al. |
| 2011/0262393 A1 | 10/2011 | Yang et al. |
| 2012/0009271 A1* | 1/2012 | Borlongan ............... A61P 25/00 424/583 |
| 2012/0269774 A1* | 10/2012 | Ichim ................... C12N 5/0087 424/93.7 |
| 2013/0130382 A1 | 5/2013 | Honmou et al. |

FOREIGN PATENT DOCUMENTS

| JP | 2012-508733 A | 4/2012 |
| JP | 2012-100662 A | 5/2012 |
| JP | 2012100662 A * | 5/2012 |
| JP | 2013-226159 A | 11/2013 |
| WO | WO 02/00849 A1 | 1/2002 |
| WO | WO 2009/034708 A1 | 3/2009 |

OTHER PUBLICATIONS

Demarin et al., Neuroplasticity. Periodicum Biologorum, vol. 116, No. 2 (2014) pp. 209-211. (Year: 2014).*
Yasuhara et al., Notch-induced rat and human bone marrow stromal cell grafts reduce ischemic cell loss and ameliorate behavioral deficits in chronic stroke. Stem Cells and Development, vol. 18, No. 10 (Dec. 2009) p. 1501-1514. (Year: 2009).*
Shen et al., Therapeutic benefit of bone marrow stromal cells administered 1 month after stroke. Journal of Cerebral Blood Flow & Metabolism, vol. 27, No. 1 (Jan. 2007) pp. 6-13. (Year: 2007).*
Supplementary European Search Report dated Oct. 17, 2019, in EP 17789738.6.
Forostyak et al., "The role of mesenchymal stromal cells in spinal cord injury, regenerative medicine and possible clinical applications," Biochimie, Aug. 27, 2013, 95(12):2257-2270.
International Search Report dated Jun. 13, 2017, in PCT/JP2017/017325.
Gutierrez-Fernandez et al., "Effects of intravenous administration of allogenic bone marrow- and adipose tissue-derived mesenchymal stem cells on functional recovery and brain repair markers in experimental ischemic stroke," Stem Cell Research & Therapy, 2013, 4:11, 1-12.
Honma et al., "Intravenous infusion of immortalized human mesenchymal stem cells protects against injury in a cerebral ischemia model in adult rat," Experimental Neurology, 2006, 199:56-66.
Honmo, O., The Hokkaido Journal of Occupation Therapy: Hokkaido Sagyo Ryoho, Feb. 2015, 32(1):13-28, with partial English translation.
Honmou et al., "Intravenous administration of auto serum-expanded autologous mesenchymal stem cells in stroke," Brain, 2011, 134:1790-1807.
Iihoshi et al., "A therapeutic window for intravenous administration of autologous bone marrow after cerebral ischemia in adult rats," Brain Research, 2004, 1007:1-9.
Nomura et al., "I.V. Infusion of Brain-Derived Neurotrophic factor Gene-Modified Human Mesenchymal Stem Cells Protects Against Injury in a Cerebral Ischemia Model in Adult Rat," Neuroscience, 2005, 136:161-169.
Matchynski-Franks et al., "Mesenchymal Stem Cells as Treatment for Behavioral Deficits and Neuropathology in the 5xFAD Mouse Model of Alzheimer's Disease," Cell Transplantation, Feb. 2, 2016, 25:687-703.

(Continued)

*Primary Examiner* — Kara D Johnson
(74) *Attorney, Agent, or Firm* — Foley & Lardner LLP

(57) ABSTRACT

The present invention relates to a synapse formation promoter and a brain plasticity promoter comprising CD24-negative mesenchymal stem cells prepared from a patient's own bone marrow aspirate and treatment of dementia, chronic-phase cerebral infarction, chronic-phase spinal cord injury, mental diseases, and the like using the synapse formation promoter and brain plasticity promoter.

11 Claims, 24 Drawing Sheets

(56) References Cited

OTHER PUBLICATIONS

Naaldijk et al., "Effect of systemic transplantation of bone marrow-derived mesenchymal stem cells on neuropathology markers in APP/PS1 Alzheimer mice," Neuropathy and Applied Neurobiology, 2017 (online Feb. 26, 2016), 43:299-314.
Office Action dated Mar. 11, 2021 in EP 17789738.6.
Office Action dated Nov. 30, 2021 in JP 2018-514748.
Oh et al., "Mesenchymal Stem Cells Increase Hippocampal Neurogenesis and Neuronal Differentiation by Enhancing the Wnt Signaling Pathway in an Alzheimer's Disease Model," Cell Transplantation, 2015 (online Mar. 7, 2014), 24:1097-1109.
Joyce et al., "Mesenchymal stem cells for the treatment of neurodegenerative disease," Regen. Med., Nov. 2010, 5(6):933-946.
Office Action dated Oct. 4, 2022 in EP 17789738.6.

* cited by examiner

SYNAPSE FORMATION AGENT

RELATED APPLICATION

This application is a National Stage application of PCT/JP2017/017325, filed Apr. 26, 2017, which claims priority from Japanese applications JP 2016-091286, filed Apr. 28, 2016 and JP 2016-091300, filed Apr. 28, 2016.

The contents of Japanese Patent Application No. 2016-091286 (filed on Apr. 28, 2016) and Japanese Patent Application No. 2016-091300 (filed on Apr. 28, 2016), to which this application claims priority, are incorporated herein.

TECHNICAL FIELD

The present invention relates to a synapse formation agent and a brain plasticity promoter comprising mesenchymal stem cells. More particularly, the present invention relates to a synapse formation agent and a brain plasticity promoter comprising CD24-negative mesenchymal stem cells prepared from a patient's own bone marrow or blood.

BACKGROUND ART

Mesenchymal stem cells (MSCs) are known to provide the protection of the brain (parenchyma and blood vessel). It is confirmed using an experimental infarction model that the MSC administration after cerebral infarction improves the behavioral function and reduces the ischemic lesion volume (Non Patent Literature 1 to 3, Patent Literature 1). Moreover, the treatment of cerebral infarction patients by intravenous administration of MSCs have been conducted many times and the improvement of motor function and lesion has been reported (Non Patent Literature 4, Patent Literature 2).

Meanwhile, intravenous administration of MSCs to patients with spinal cord injury has been found to cause functional recovery, promotion of axon regeneration, and reduction of damage sites. Although there have been many reports of the effect of MSCs on patients in the acute phase of spinal cord injury so far, studies on patients in the chronic phase are limited and the effect of MSCs has not been confirmed enough.

For the therapeutic mechanism of MSCs, many mechanisms of action have been supposed and these are classified into three categories: neurotrophic and protective effects of neurotrophic factors, angiogenesis effect (restoration of the cerebral blood flow), and nerve regeneration. The neurotrophic and protective effects are expected to be mediated by humoral factors such as the neurotrophic factors brain derived neurotrophic factor (BDNF) and glial derived neurotrophic factor (GDNF). The angiogenesis effect is considered to involve two mechanisms: one is the secretion of angiogenesis factors by MSCs accumulated in the lesion to induce angiogenesis and the other one is differentiation of administered MSCs themselves into vascular endothelia to form new blood vessels. The nerve regeneration effect is also considered to involve two mechanisms: one is the promotion of endogenous neurogenesis by MSCs accumulated in the lesion and the other one is differentiation of administered MSCs themselves into nerve cells and glial cells.

However, the above-mentioned mechanisms of action are only supposition from observed phenomena and no mechanism by which cerebral infarction and spinal cord injury are treated by intravenous administration of MSCs has been demonstrated.

CITATION LIST

Patent Literature

[Patent Literature 1]
WO2002/000849
[Patent Literature 2]
WO2009/034708

Non Patent Literature

[Non Patent Literature 1]
Iihoshi S. et al., Brain Res. 2004, 1007:1-9.
[Non Patent Literature 2]
Nomura T. et al., Neuroscience. 2005, 136:161-169.
[Non Patent Literature 3]
Honma T. et al., Exp. Neurol. 2006, 199:56-66.
[Non Patent Literature 4]
Honmou O. et al., Brain. 2011, 134:1790-1807.

SUMMARY OF INVENTION

Technical Problem

An object of the present invention is to provide a new method for treating an intractable neurological disease that has conventionally been considered to be difficult to treat by elucidating a therapeutic mechanism of mesenchymal stem cells (MSCs) and constructing the rationale for clinical applications thereof.

Solution to Problem

The inventors have demonstrated that intravenously administered MSCs reach the hippocampus, differentiate into nerve cells, and form synapses. They have also demonstrated that administration of MSCs in a cerebral infarction model activates not only motor and sensory areas in the infarction region but also contralesional motor and sensory areas. Furthermore, they have demonstrated that administration of MSCs in a vascular dementia model rat improves the cognitive function.

Accordingly, the present invention relates to the following (1) to (14).
(1) A synapse formation agent comprising CD24-negative mesenchymal stem cells derived from human bone marrow or blood.
(2) The synapse formation agent according to (1) above, wherein the cells are positive for at least one or more selected from CD73, CD90, CD105, and CD200 and/or negative for at least one or more selected from CD19, CD34, CD45, CD74, CD79α, and HLA-DR.
(3) The synapse formation agent according to (1) or (2) above, wherein the human bone marrow or blood is bone marrow or blood of a patient receiving administration of the synapse formation agent.
(4) The synapse formation agent according to any one of (1) to (3) above, wherein the cells have been proliferated and enriched in a medium containing human serum.
(5) The synapse formation agent according to (4) above, wherein the human serum is autologous serum of a patient receiving the synapse formation agent.
(6) The synapse formation agent according to any one of (1) to (5) above, wherein the agent is a formulation for intravenous administration, a formulation for lumber puncture administration, a formulation for intracerebral administration, a formulation for intracerebroventricular administration, a formulation for local administration, or a formulation for intraarterial administration.

(7) The synapse formation agent according to any one of (1) to (6) above, wherein the agent is a formulation for intravenous administration.

(8) The synapse formation agent according to any one of (1) to (7) above, wherein the agent is administered to a patient with dementia, a chronic phase of cerebral infarction, a chronic phase of spinal cord injury, or a mental disease.

(9) The synapse formation agent according to any one of (1) to (8) above, wherein the agent promotes brain plasticity.

(10) The synapse formation agent according to any one of (1) to (9) above, wherein an anticoagulant is heparin, a heparin derivative, or a salt thereof.

(11) The synapse formation agent according to (9) above, wherein the cells have been proliferated and enriched in a medium containing no anticoagulant or an anticoagulant at less than 0.02 U/mL.

(12) The synapse formation agent according to (10) or (11) above, wherein the human bone marrow or blood has been prepared such that an amount of the anticoagulant added at the time of collection is less than 0.2 U/mL based on the volume of the bone marrow or blood.

(13) A brain plasticity promoter comprising CD24-negative mesenchymal stem cells derived from human bone marrow or blood.

(14) The synapse formation agent according to any one of (1) to (12) or brain plasticity promoter according to (13) above, wherein the agent or the promoter is administered several times.

Advantageous Effects of Invention

According to the present invention, it has been demonstrated that intravenously administered MSCs ameliorate neurological diseases such as cerebral infarction and vascular dementia by forming synapses and rebuilding neural circuits as well as promoting brain plasticity. According to the present invention, it is indicated that administration of MSCs is effective for dementia (vascular dementia, Alzheimer-type dementia), intractable neurological diseases such as chronic-phase cerebral infarction and chronic-phase spinal cord injury, and mental diseases, which have conventionally been considered to be difficult to treat and the effect restores not only the motor function but also higher functions such as memory impairment.

In any of the three tests (A: water maze test, B: novel object recognition test, C: novel object placement test) for the cognitive functions, the MSC administration group indicated improvement of cognitive functions in comparison with the control group.

Figure 5:
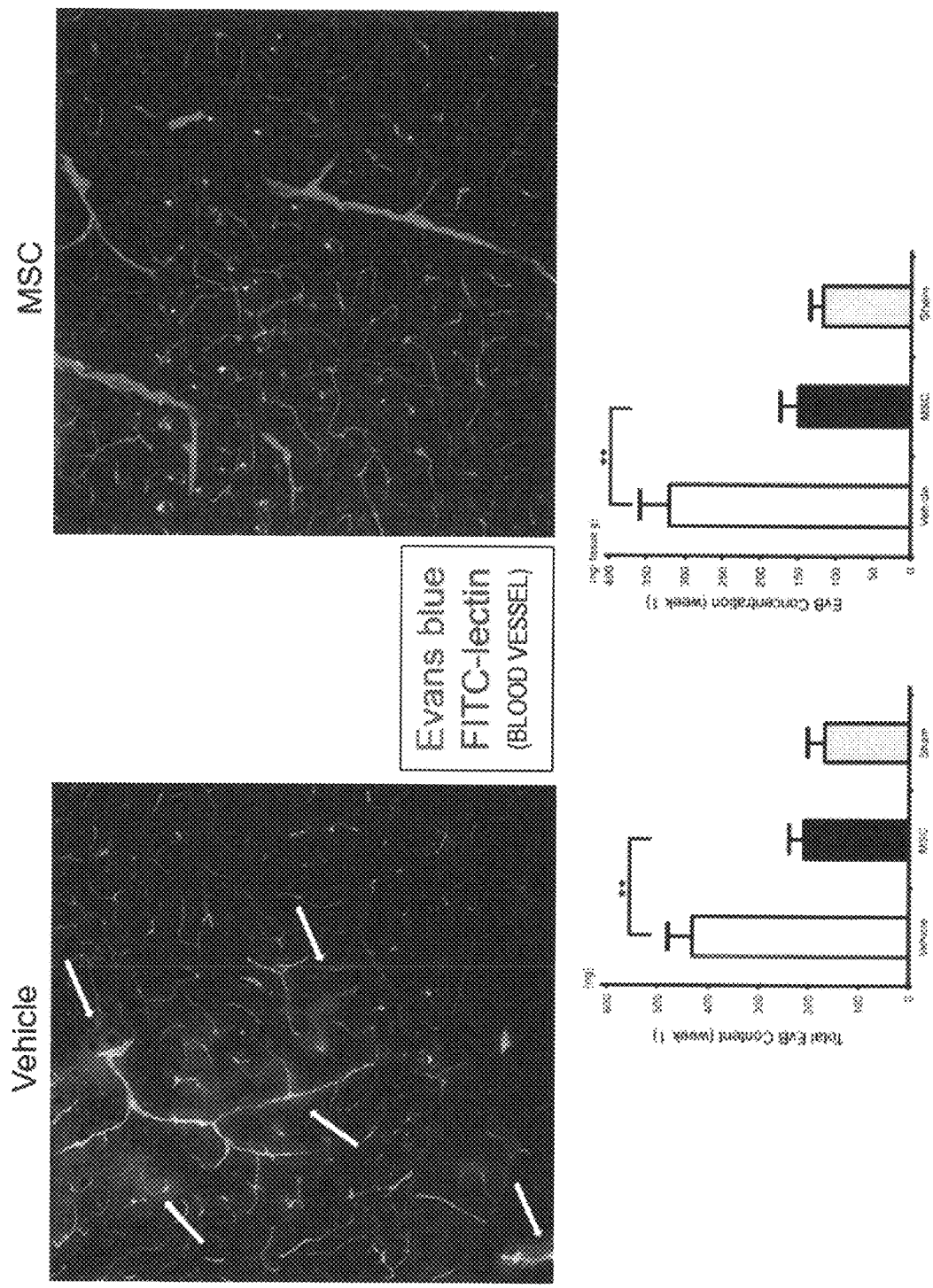

FIG. 5 illustrates the evaluation of the blood-brain barrier with Evans Blue.

In the control, Evans Blue (red), which should remain in the blood vessels in the normal brain, is leaked out from the blood vessels to the outer tissue (left), which is ameliorated in the administration of MSCs (right).

Figure 6:
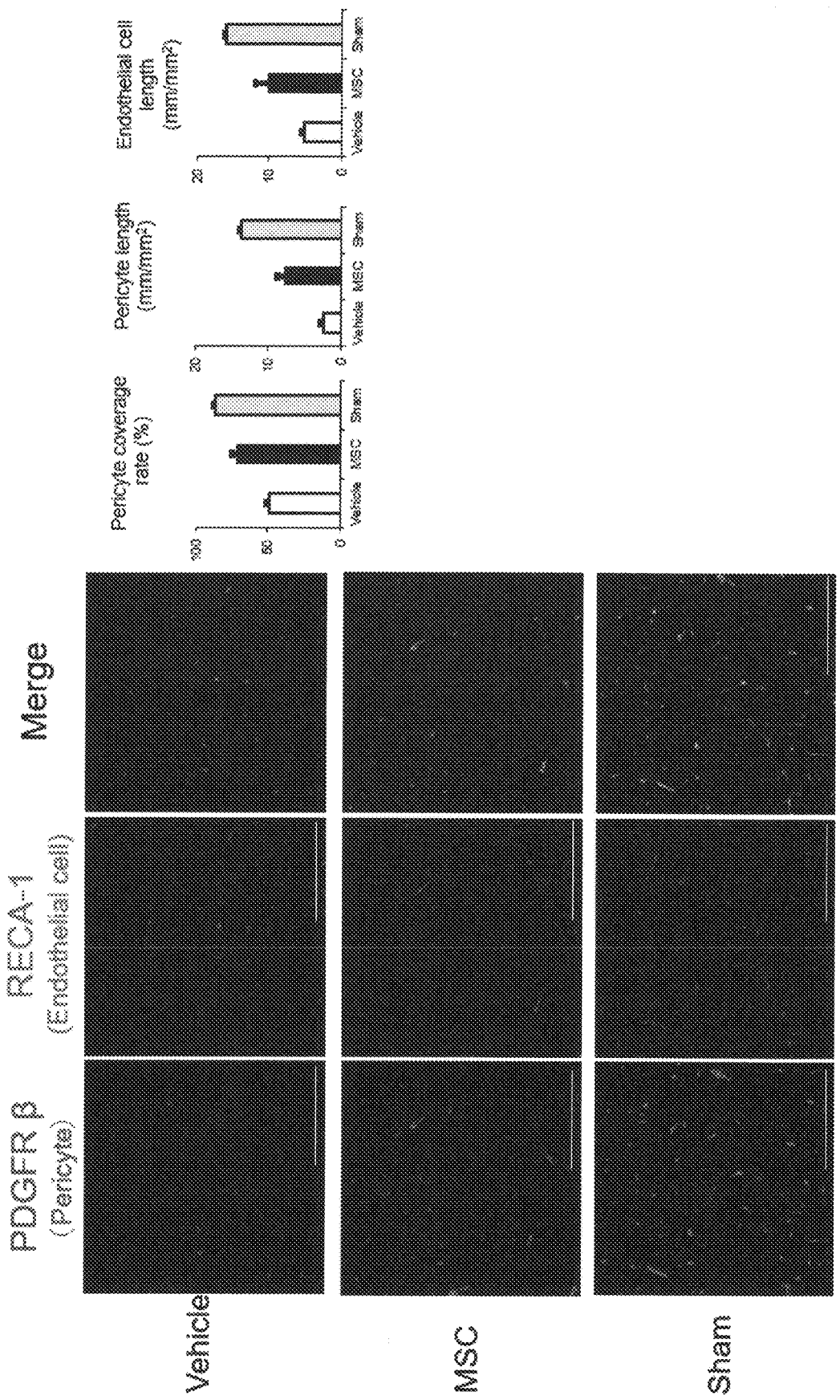

FIG. 6 illustrates increase of pericytes and endothelial cells by the administration of MSCs in the blood-brain barrier.

(Left) The left panels indicate the expression of PDGFRβ (pericyte marker) and RECA-1 (endothelial cell marker). (Right) A: Pericyte coverage rate, B: Pericyte-positive blood vessel length, C: Vascular endothelium length.

Figure 7:
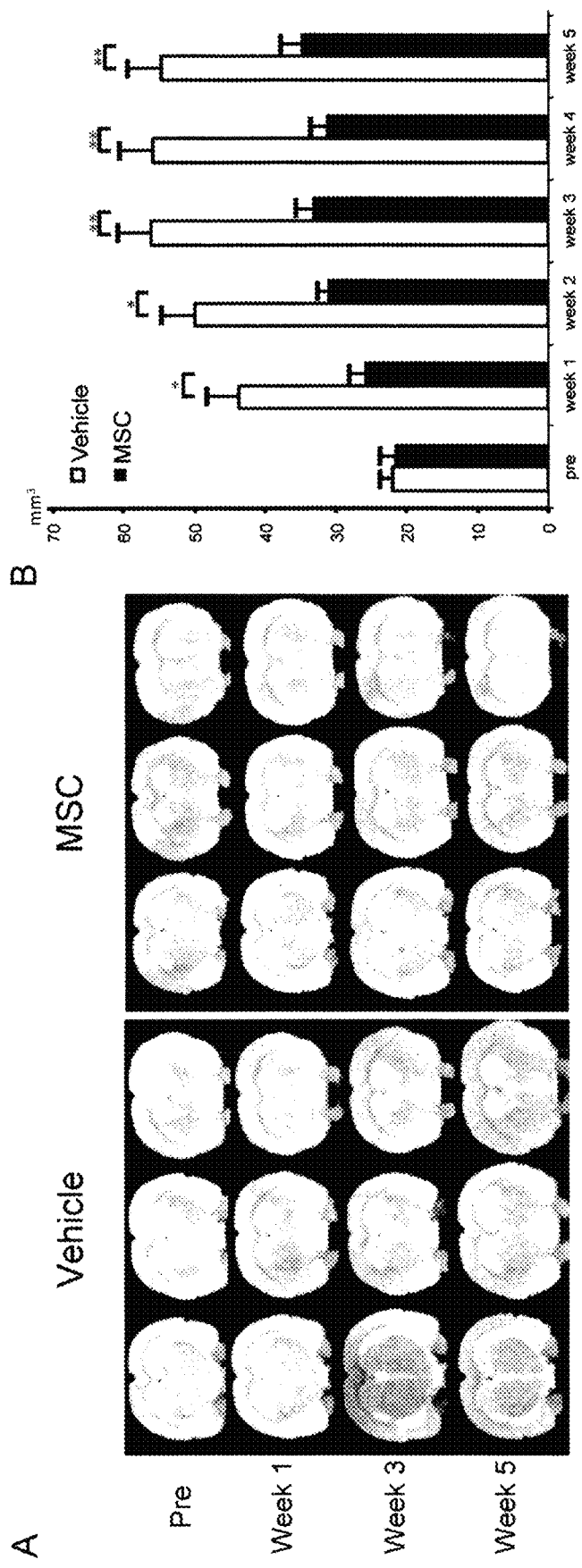

FIG. 7 illustrates the evaluation of volume of the lateral ventricle by MRIT2.

A: Weighted images before infarction (Pre), on week 1, week 3, and week 5 (left: Control, right: MSC administration). B: Lateral ventricle volumes before infarction and on week 1 to week 5.

Figure 8:
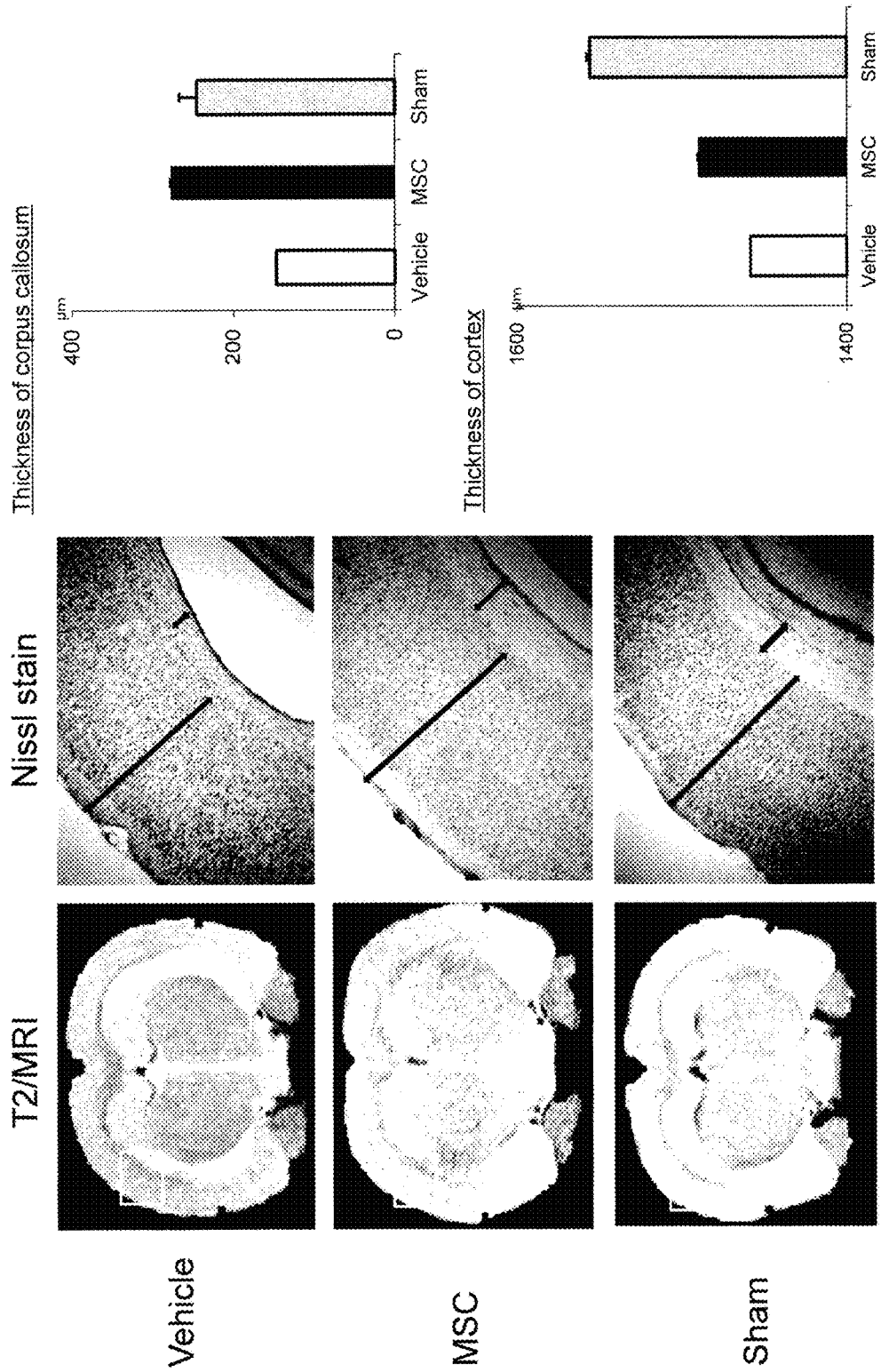

FIG. 8 illustrates the thickness of cerebral cortex and corpus callosum.

(Left) Weighted images and Nissl staining images (from the top, Control, MSC administration, Sham (no treatment)). (Right) Top: thickness of corpus callosum, Bottom: thickness of cerebral cortex (from the left, Control, MSC administration, Sham (no treatment)).

Figure 9:
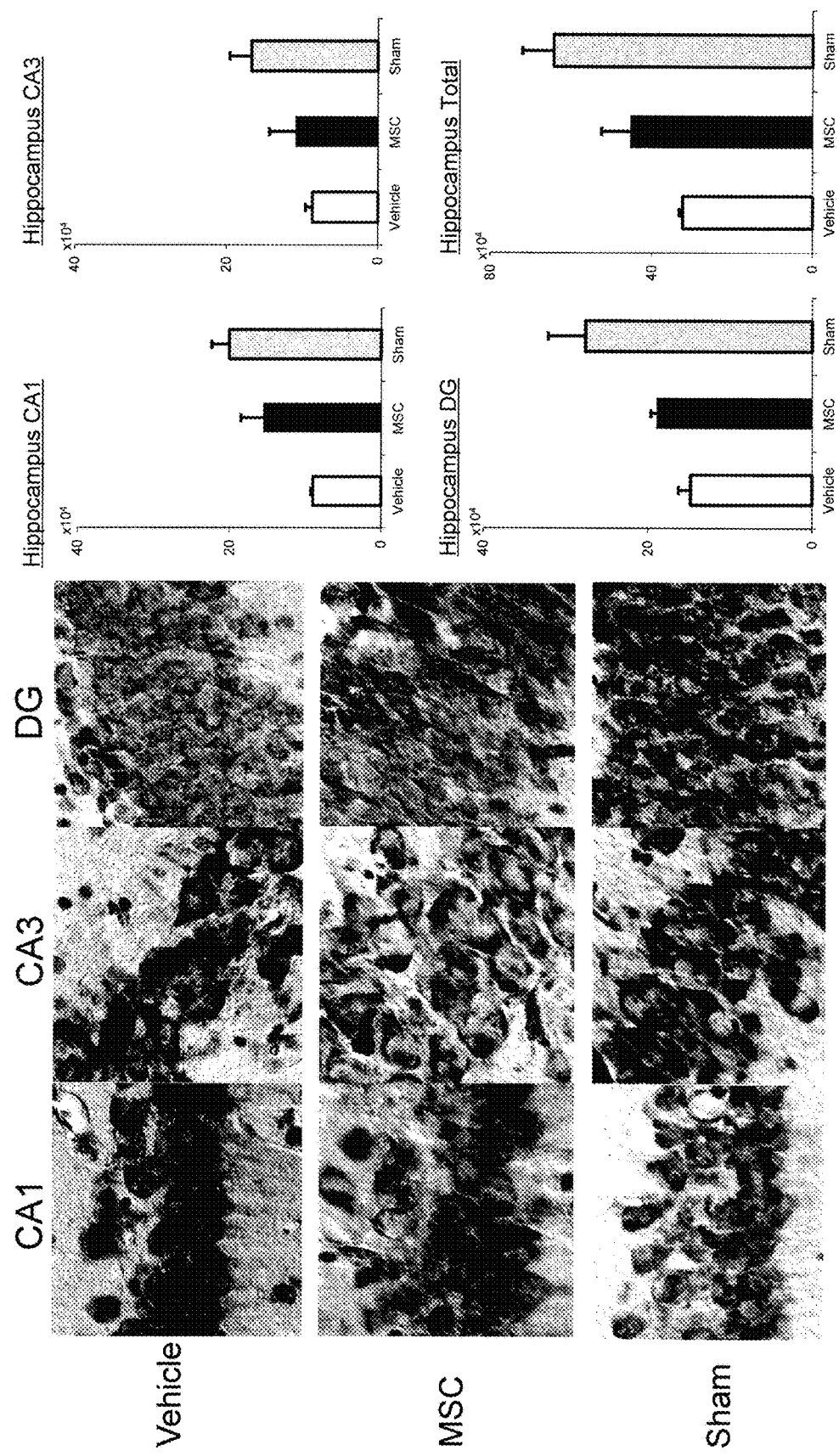

FIG. 9 illustrates nerve cell counts in the hippocampus. By the administration of MSCs, the nerve cell count in the hippocampus is also improved.

CA1 (Vehicle: $8.95+/-0.38 \times 10^4$, MSC: $15.53+/-4.18 \times 10^4$, No treatment: $20.04+/-4.81 \times 10^4$), CA3 (Vehicle: $8.61+/-1.31 \times 10^4$, MSC: $10.85+/-4.86 \times 10^4$, No treatment: $16.68+/-5.8 \times 10^4$), DG (Vehicle: $14.89+/-2.07 \times 10^4$, MSC: $19.01+/-0.96 \times 10^4$, No treatment: $27.61+/-9.10 \times 10^4$), Total (Vehicle: $32.47+/-1.14 \times 10^4$, MSC: $45.41+/-10.00 \times 10^4$, No treatment: $64.33+/-15.49 \times 10^4$)

Figure 10:
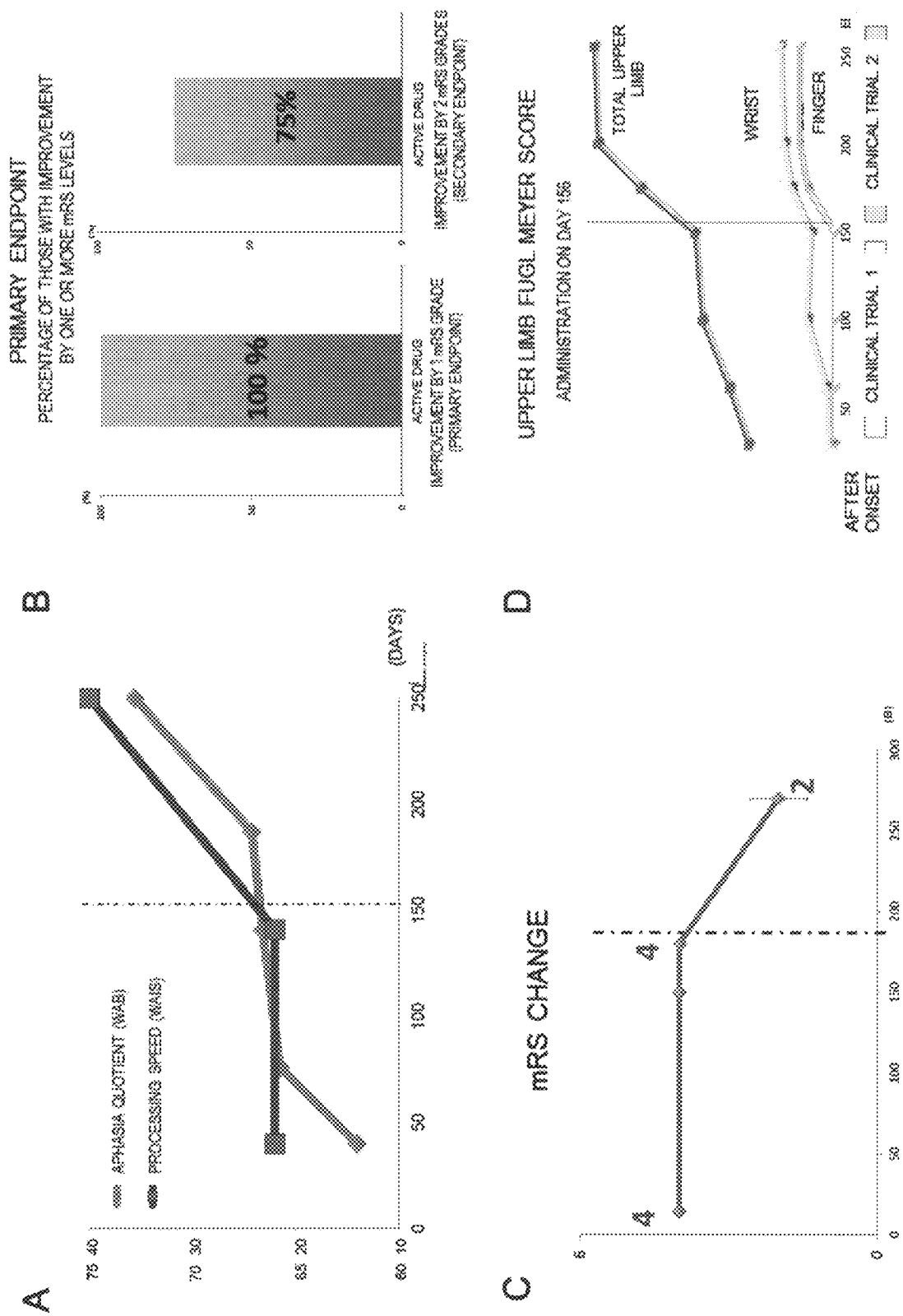

FIG. 10 illustrates the effect of the administration of MSCs on patients with chronic-phase cerebral infarction. A: The graph illustrates the improvement of higher functions (♦: Aphasia quotient, ■: Processing speed). B, C: The graphs illustrate the improvement in mRS. D: The graph illustrates the improvement in the FUGL MEYER score.

Figure 11:
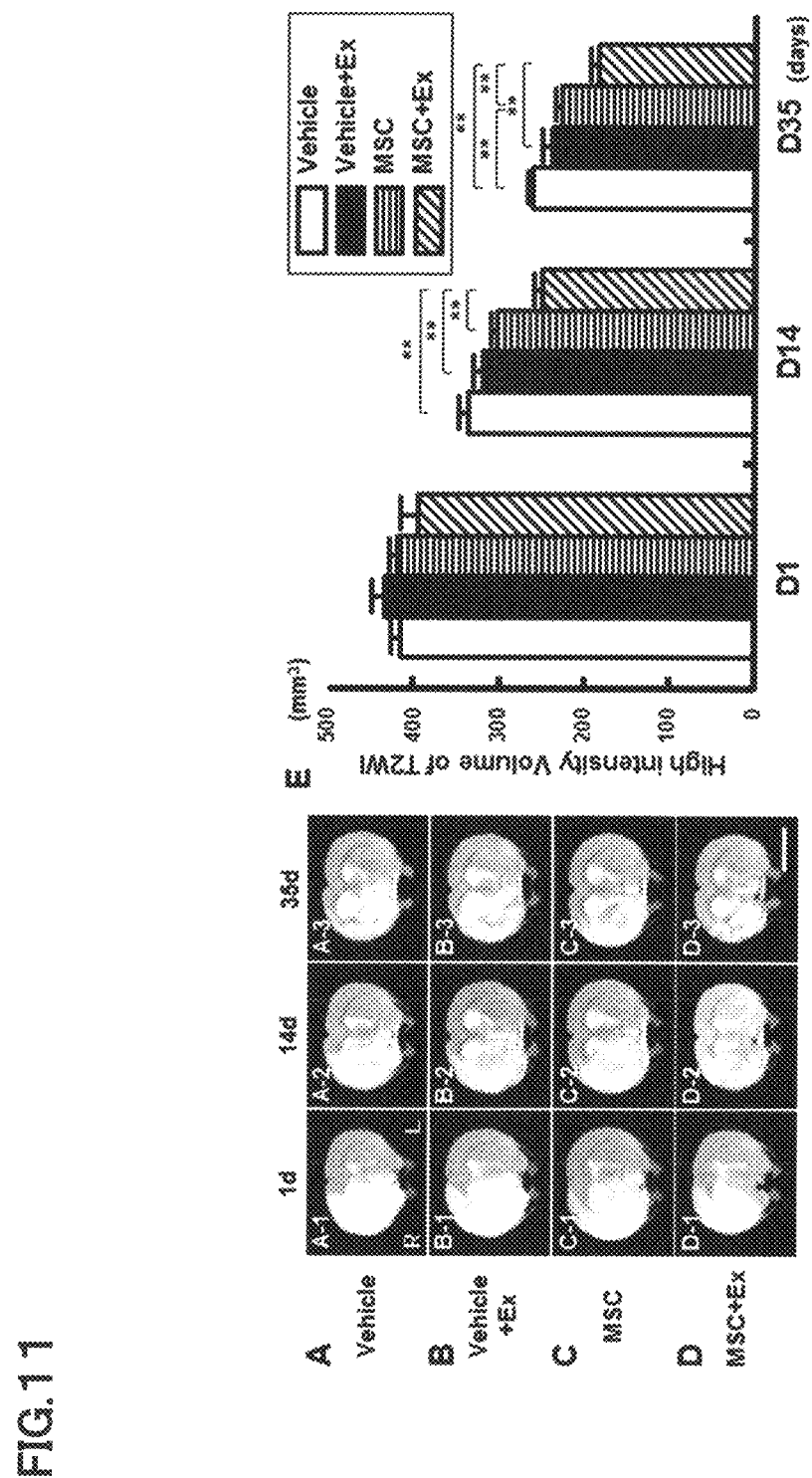

FIG. 11 illustrates the effect of rehabilitation combined with MSC transplant.

A: Vehicle administration, B: Vehicle administration+ Exercise (rehabilitation), C: MSC, D: MSC administration+ Exercise, E: Volume of high signal region on day 1, day 14, day 35. The bars represent A to D in the order from the left.

Figure 12:
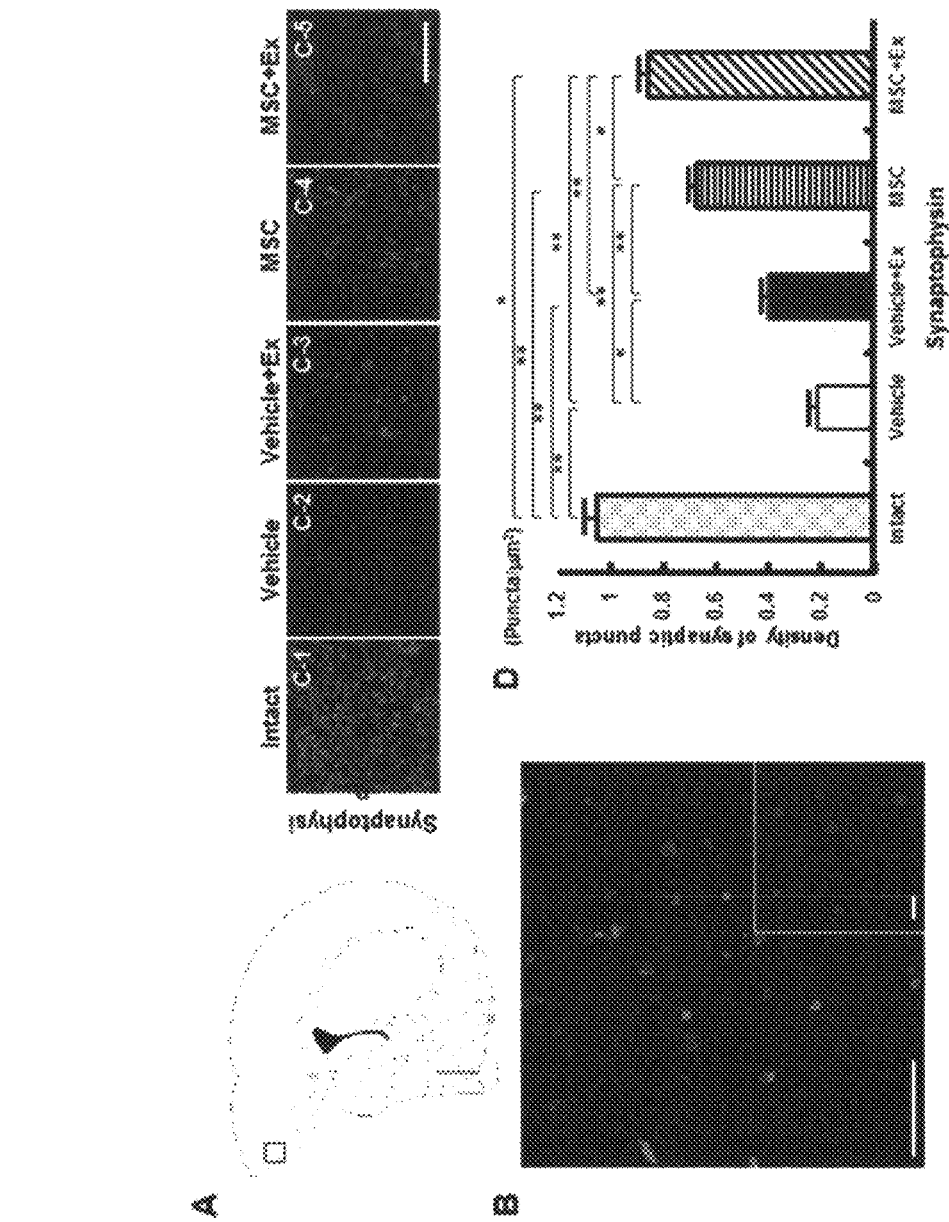

FIG. 12 illustrates the effect of rehabilitation combined with MSC transplant.

A: Schema, B: Image of the accumulation of transplant cells (green), C: Immunostaining of the synapse, D: Synapse density (from the left side of the graph, No treatment, Vehicle administration, Vehicle administration+Exercise, MSC administration, MSC administration+Exercise).

Figure 13:
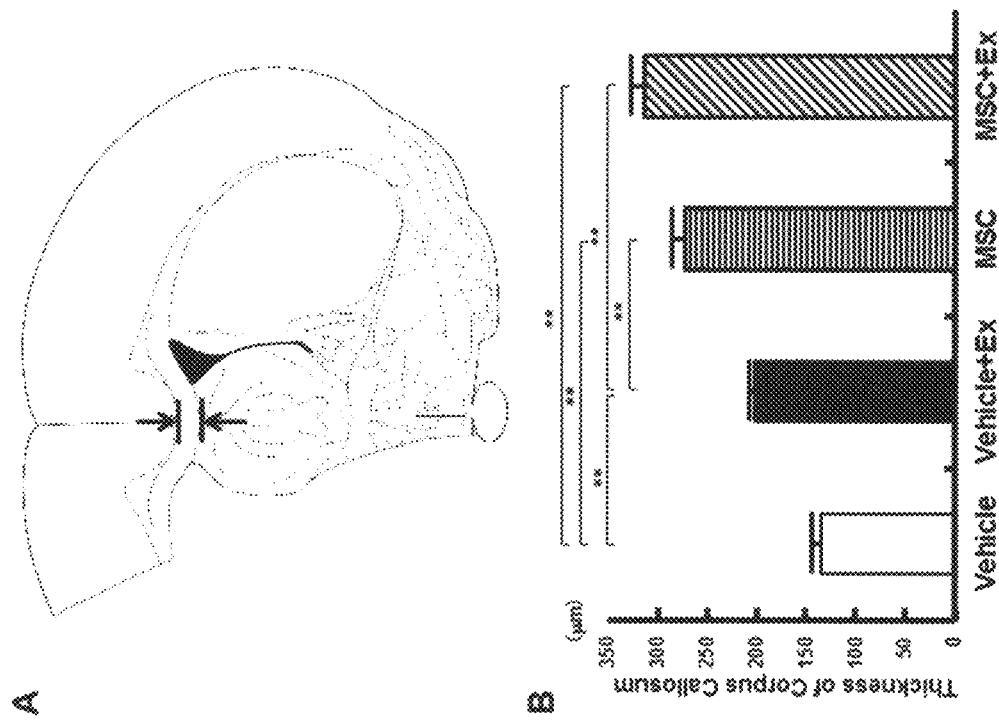

FIG. 13 illustrates the effect of rehabilitation combined with MSC transplant.

A: Measured position of corpus callosum, B: Thickness of corpus callosum (from the left side of the graph, Vehicle administration, Vehicle administration+Exercise, MSC administration, MSC administration+Exercise).

Figure 14:
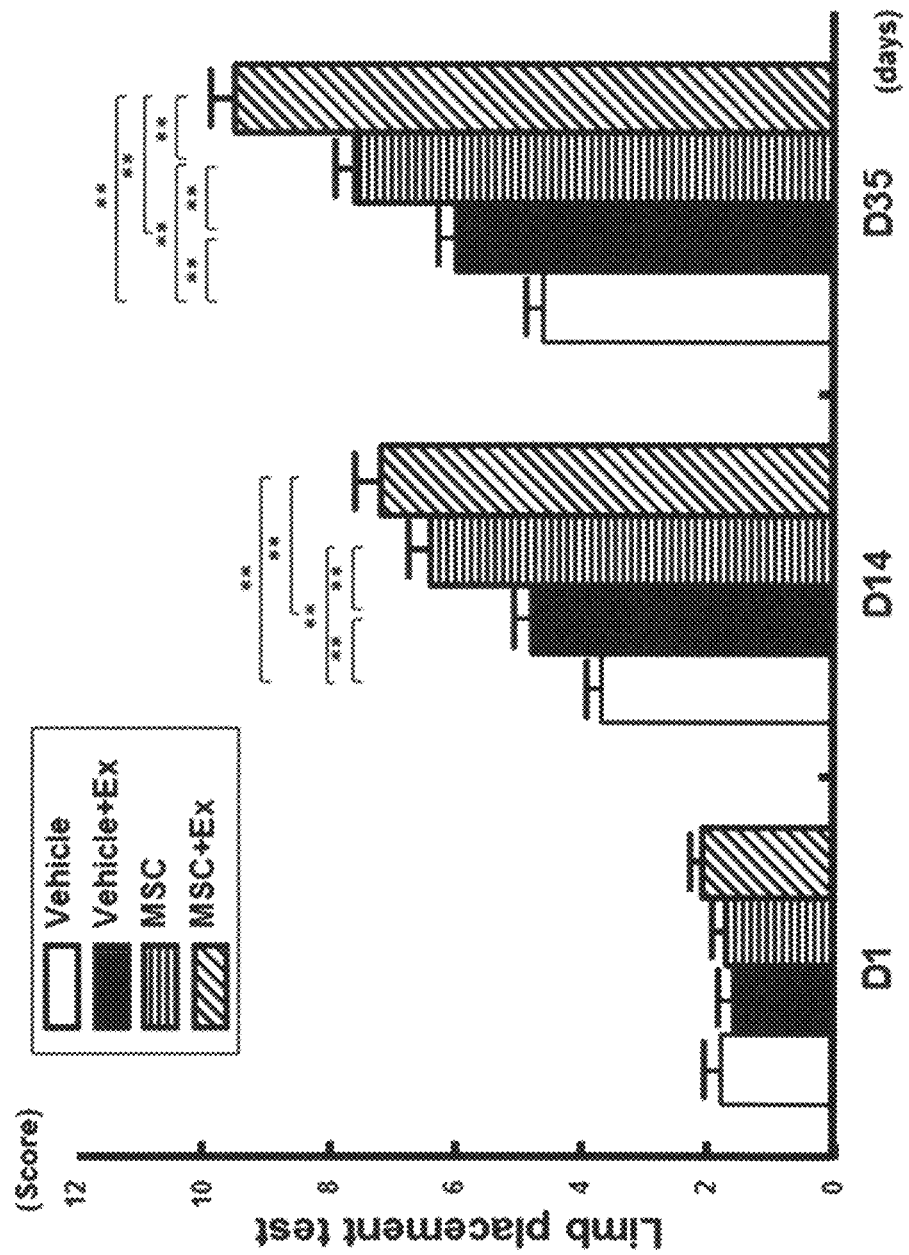

FIG. 14 illustrates the effect of rehabilitation combined with MSC transplant.

Results of Limb Placement Test on day 1, day 14, day 35 (from the left side of the graph, Vehicle administration, Vehicle administration+Exercise, MSC administration, MSC administration+Exercise).

Figure 15:
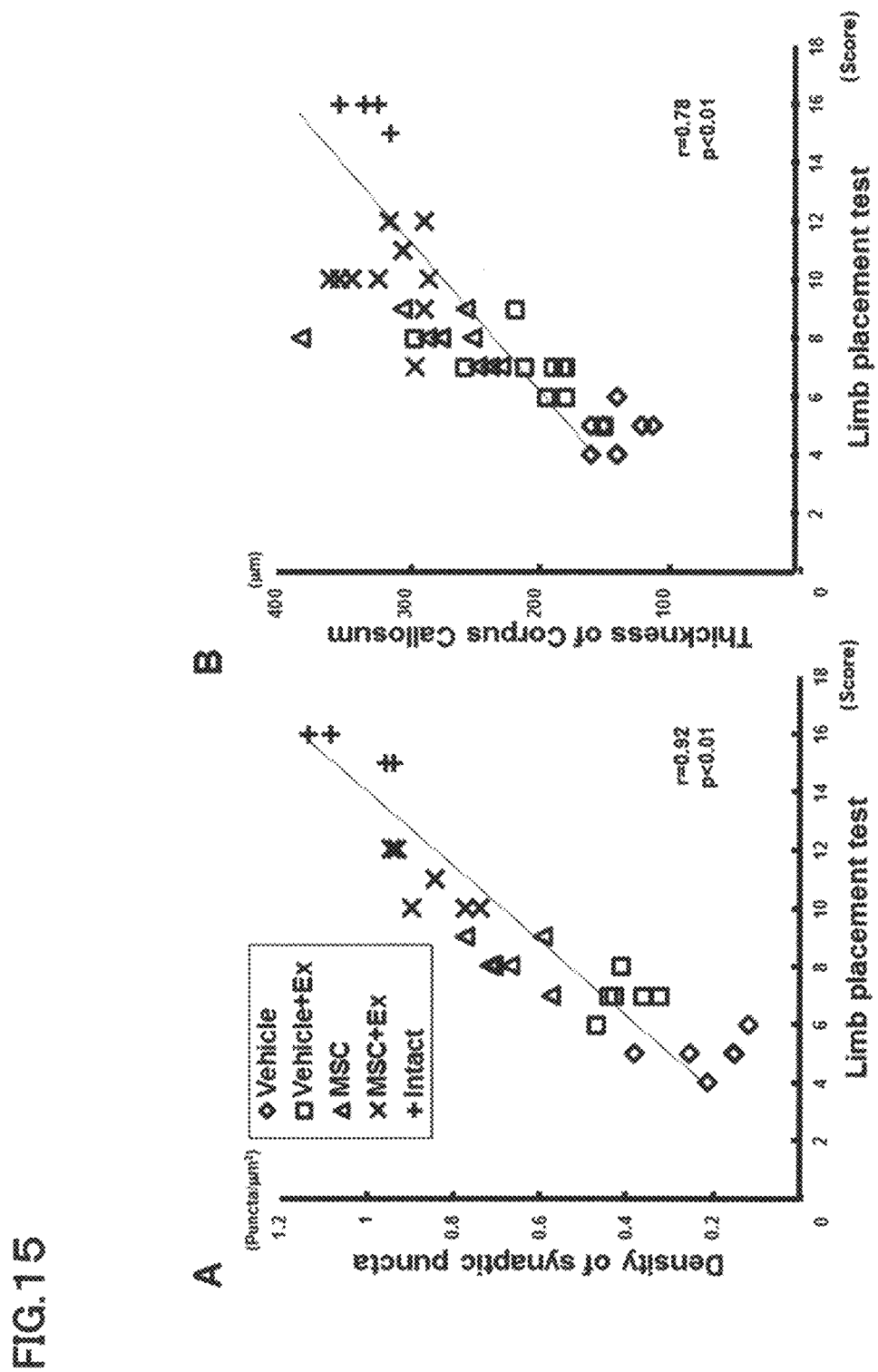

FIG. 15 illustrates the relation between a motor behavior index and the therapeutic effect when rehabilitation is combined with the MSC transplant.

A: There is a positive correlation between the motor behavior index (Limb Placement Test) and the synapse density. B: There is a positive correlation between the motor behavior index (Limb Placement Test) and the thickness of corpus callosum.

Figure 16:
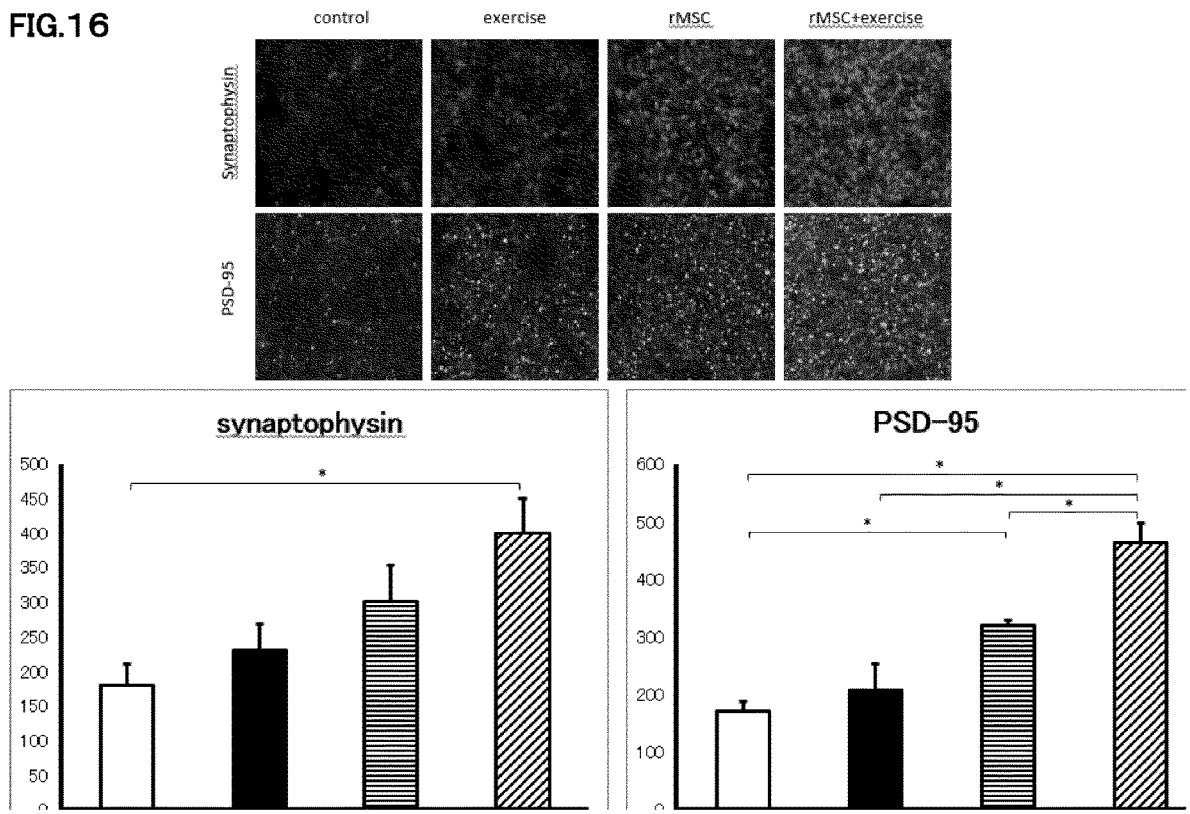

FIG. 16 illustrates the combinational effect of the MSC transplant and rehabilitation on brain plasticity.

The expression levels of synaptophysin (left) and PSD-95 (right) in the cortex. The bars represent control, exercise, MSC administration, and MSC administration+exercise from the left side of the graph. There are the pre-synapse (left) and post-synapse (right) effects also in the cortex of the side not affected by infarction (normal).

Figure 17:
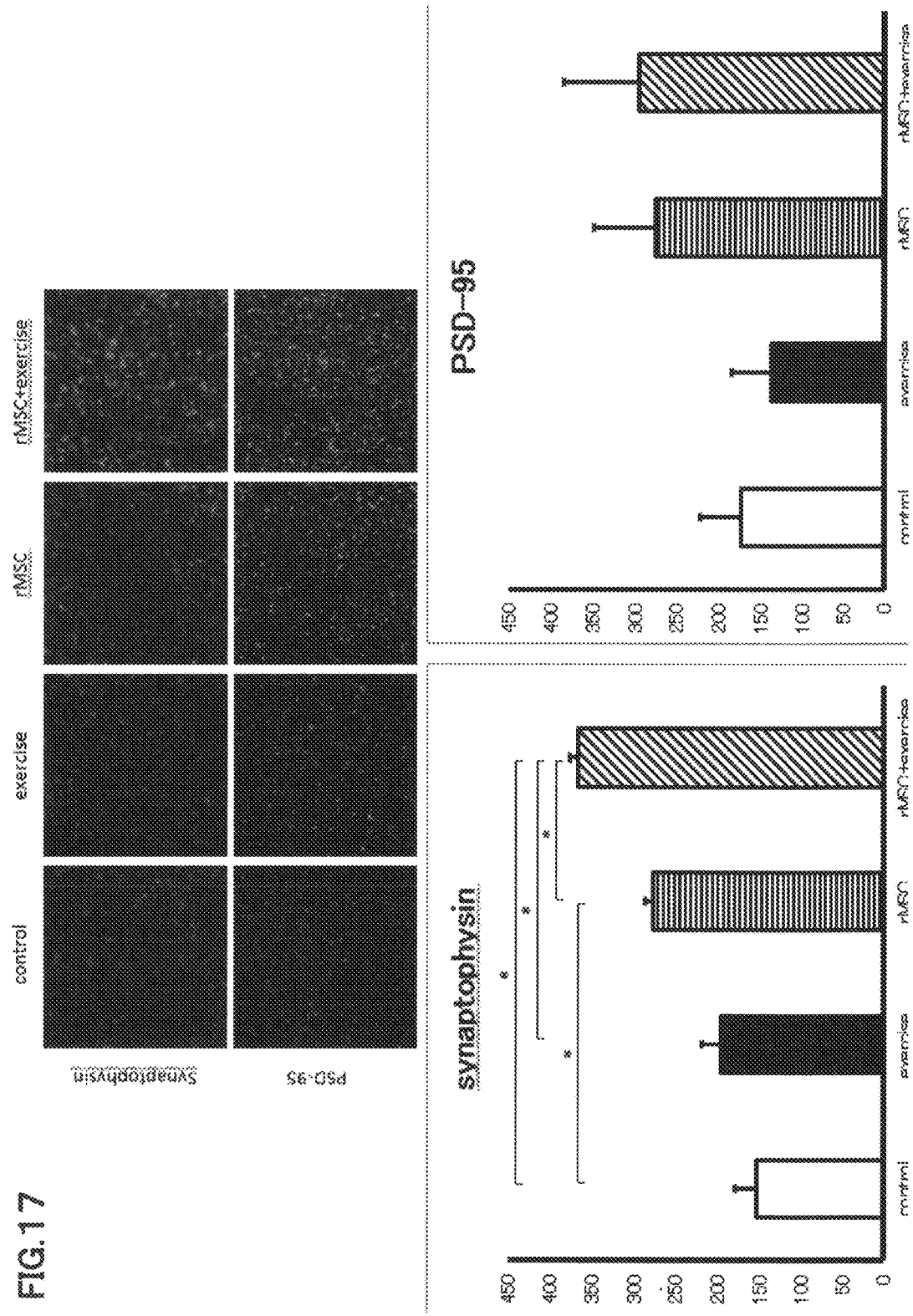

FIG. 17 illustrates the combinational effect of rehabilitation and the MSC transplant on brain plasticity.

The expression levels of synaptophysin (left) and PSD-95 (right) in the striatum. The bars represent control, exercise, MSC administration, and MSC administration+exercise from the left side of the graph. There are the pre-synapse (left) and post-synapse (right) effects also in the cortex of the side not affected by infarction (normal).

Figure 18:
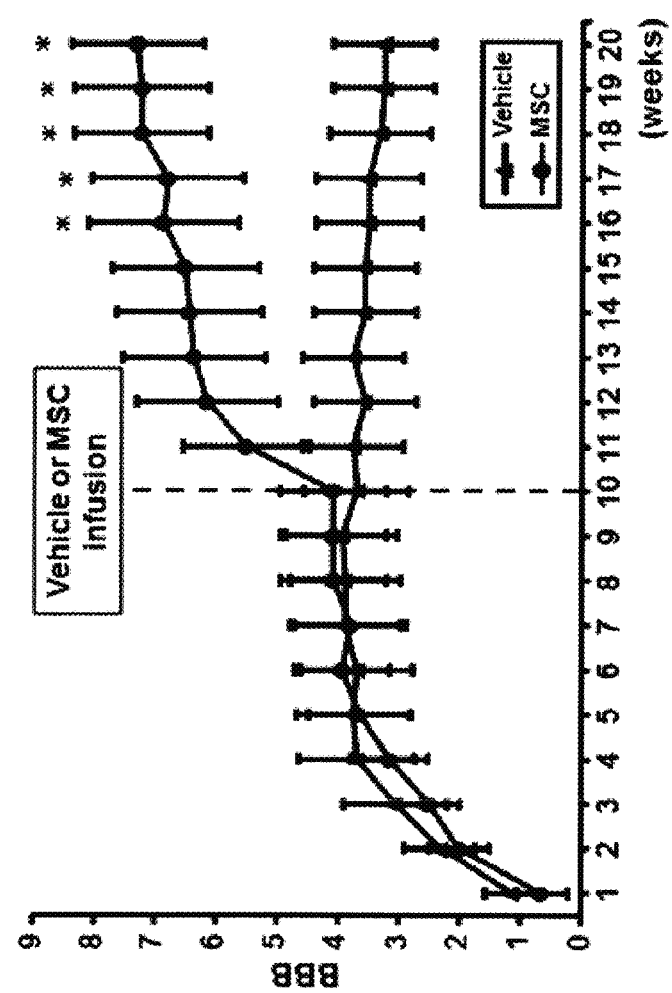

FIG. 18 illustrates a behavioral assessment of rats with chronic spinal cord injury (▲: Vehicle, ●: MSC).

Figure 19:
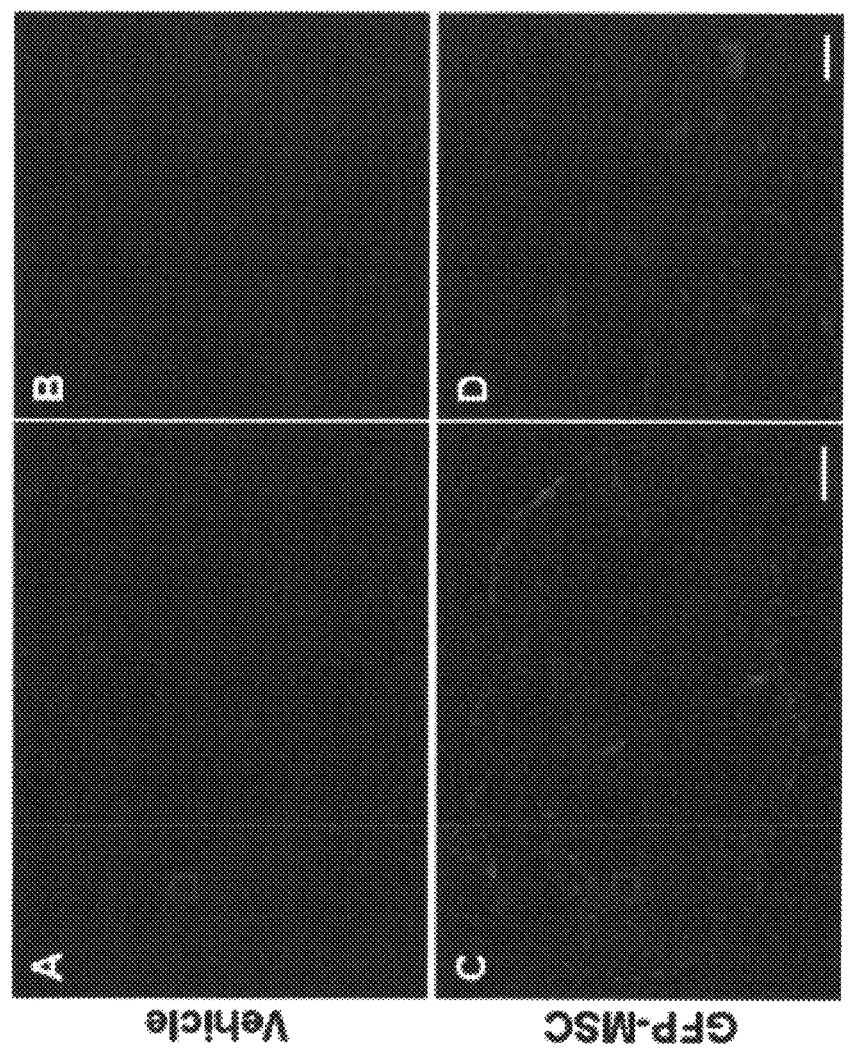

FIG. 19 illustrates the localization of GFP-MSCs administered to rats with chronic spinal cord injury. About 8.6% are localized in the damage site.

Figure 20:
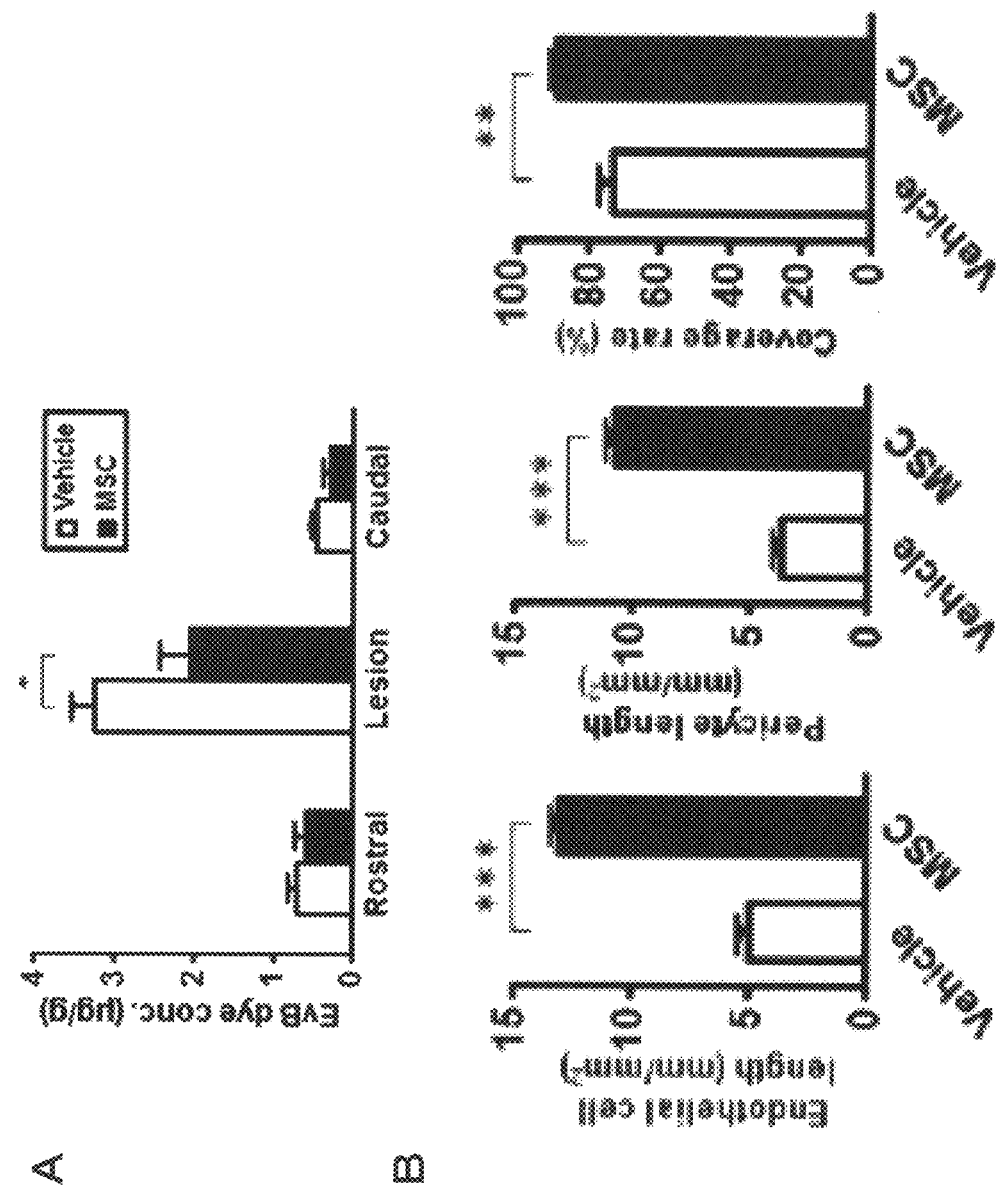

FIG. 20 illustrates the result of analysis with Evans Blue in rats with chronic spinal cord injury. A: Result of the evaluation with Evans Blue, B: Vascular endothelium length, Pericyte-positive blood vessel length, Pericyte coverage rate, from the left.

Figure 21:
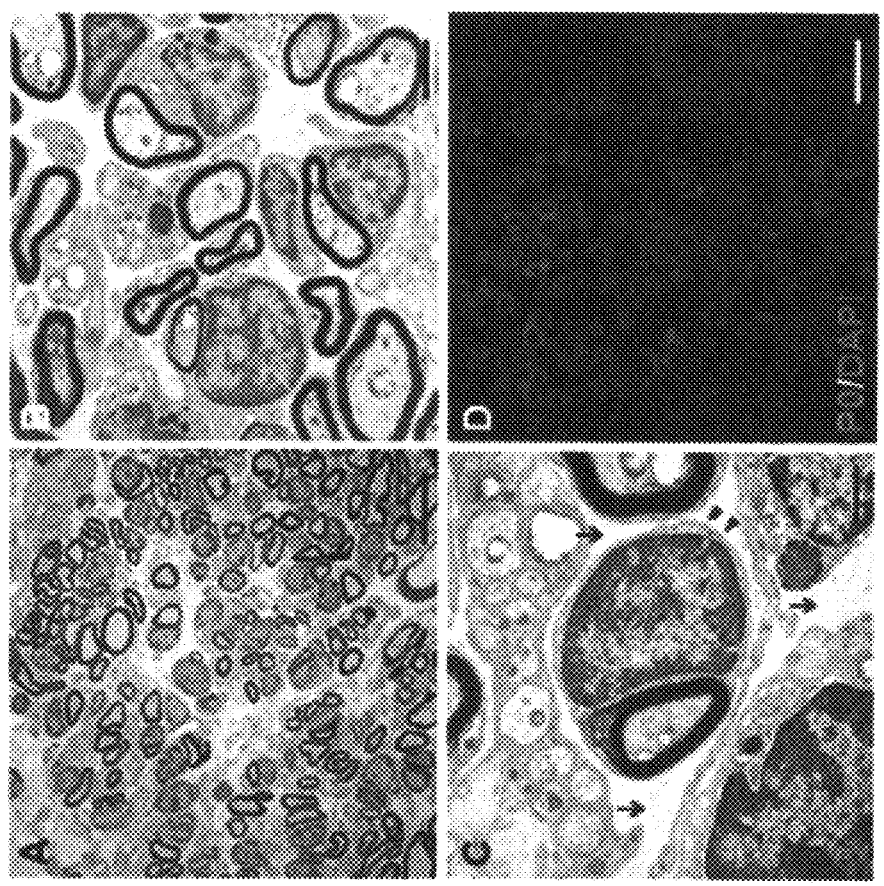
Figure 21:
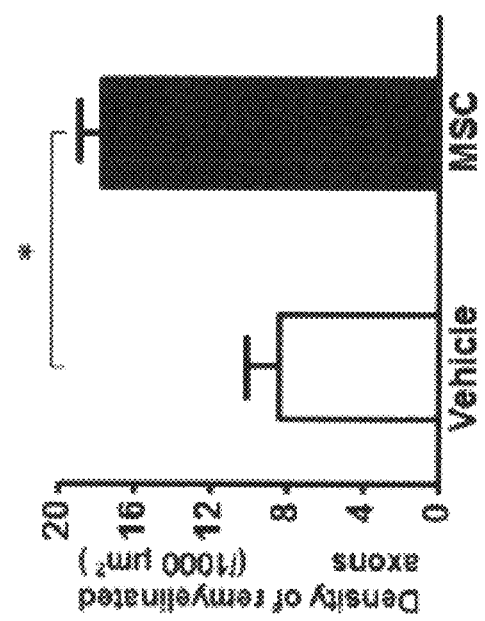

FIG. 21 illustrates the result of analysis using an anti-P0 antibody in rats with chronic spinal cord injury. A: Remyelinated axons, B, C: Electron microscope images, D: Immunostaining image with anti-P0 antibody.

Figure 22:
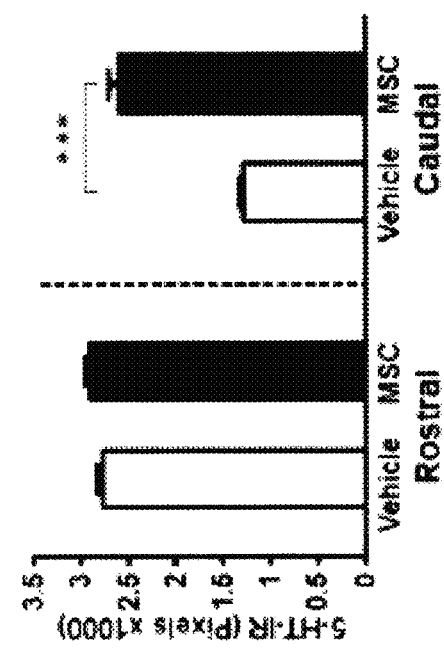
Figure 22:
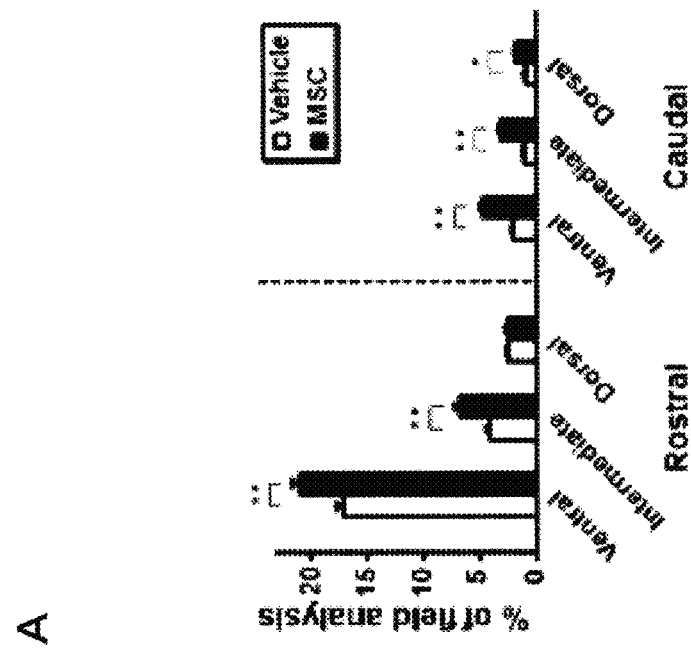

FIG. 22 illustrates the result of immunostaining in rats with chronic spinal cord injury. A: Result of immunostaining of the corticospinal tract in the posterior column of the spinal cord with rabbit anti-protein kinase C-γ, B: Result of 5-HT immunostaining of the extrapyramidal tract.

Figure 23:
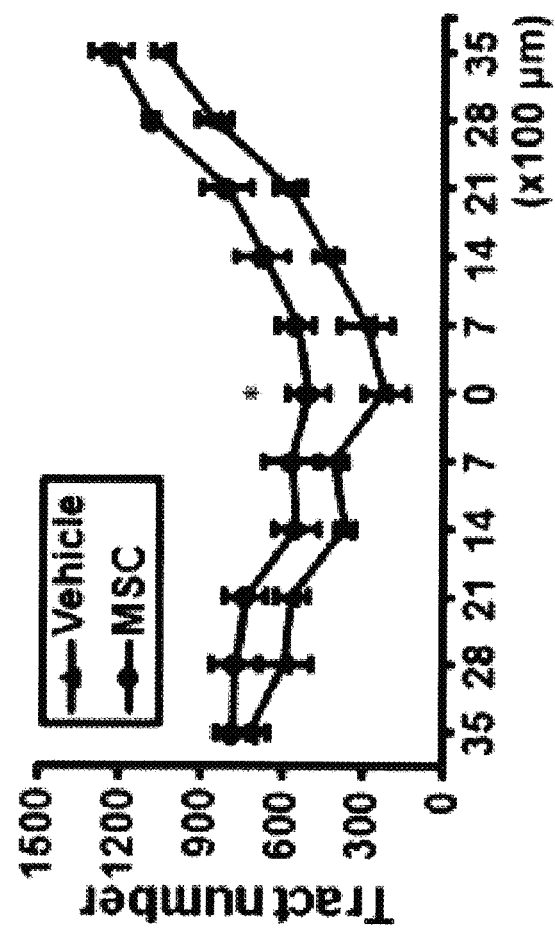

FIG. 23 illustrates the result of DTI analysis of nerve fiber bundles in rats with chronic spinal cord injury.

Figure 24:
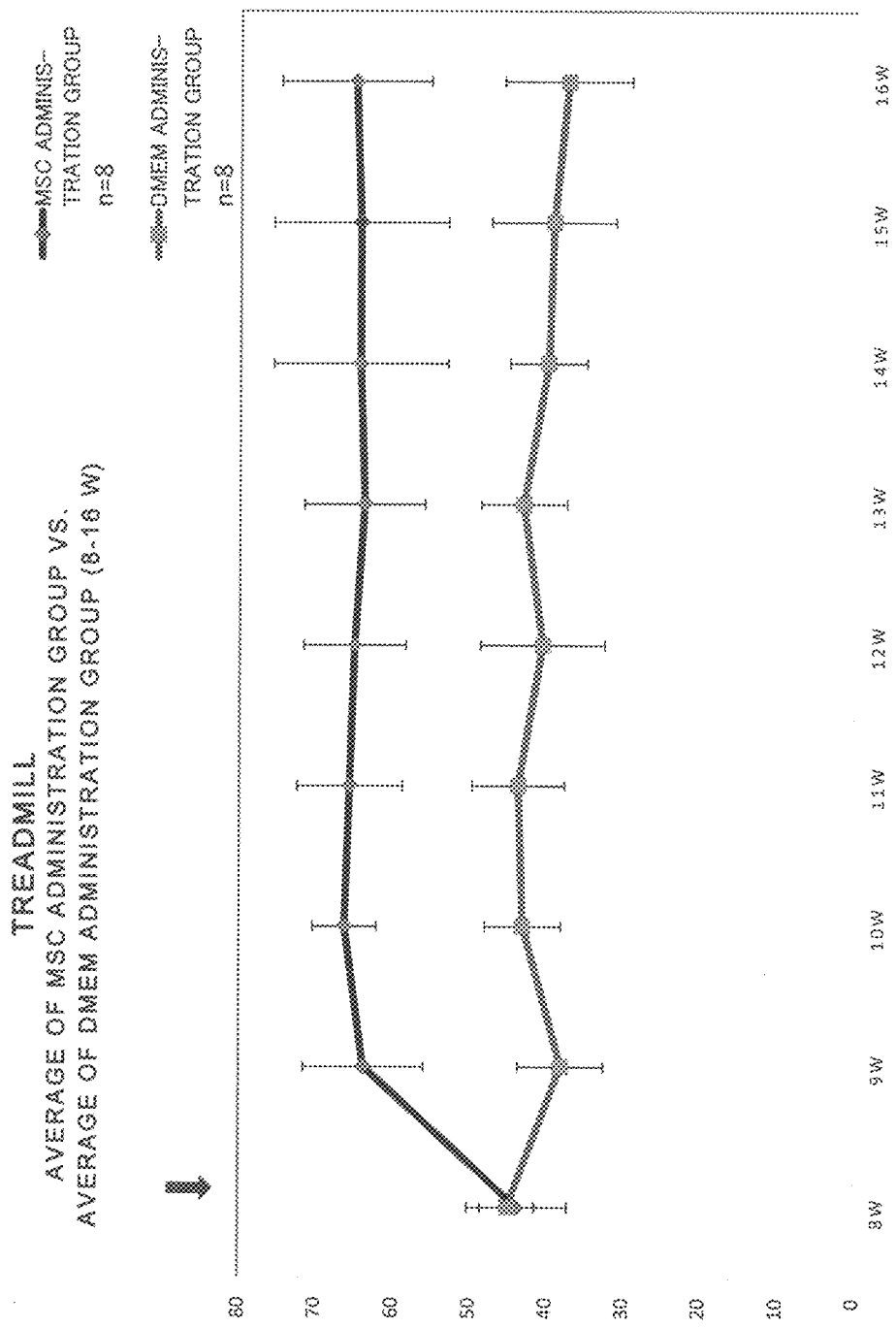

FIG. 24 illustrates improvement in motor function by the administration of MSCs in chronic-phase cerebral infarction model rats.

DESCRIPTION OF EMBODIMENTS

[Synapse Formation Agent]

The "synapse formation agent" according to the present invention is a cellular preparation containing CD24-negative mesenchymal stem cells (MSCs) derived from human bone marrow or blood and is a medicament having the effect of rebuilding neural circuits, since the administered MSCs reach the affected portion, differentiate into nerve cells, and form synapses. As described below, the synapse formation agent according to the present invention has the effect of promoting brain plasticity.

The nerve cell has a structure in which dendrites and an axon extend from a cell body having a nucleus and the dendrites receive signals from other cells and the axon sends signals to other cells. The synapse is a minute gap between an axon terminal of a nerve cell and a dendrite of another nerve cell and has an important role as a signaling junction of the nerve cell. The "synapse formation" is a process in which an axon extending from a nerve cell appropriately elongates to the vicinity of a target cell with which the nerve cell is to establish a neural connection and reaches the target to form a synapse between the axonal terminal and the target cell and is an important process for forming a correct neural circuit.

[Brain Plasticity Promoter]

The present invention also provides a brain plasticity promoter comprising CD24-negative mesenchymal stem cells (MSCs) derived from human bone marrow or blood.

The phenomenon in which nerve cells and/or brain circuits make up the optimal processing system according to the environment or a need is referred to as the "brain plasticity." The MSCs according to the present invention also have the function of promoting the "brain plasticity" with which sites that have not been damaged function beyond usual ranges to compensate the function of the damage sites. Accordingly, intravenously administered MSCs exhibit the therapeutic effect for neurodegenerative diseases such as dementia, cerebral infarction, spinal cord injury, and Parkinson's disease by promoting reconstruction of neural circuits by the synapse formation as well as promoting brain plasticity.

[Mesenchymal Stem Cells]

The "mesenchymal stem cells" used in the present invention are stem cells having multipotency and the self-renewal present in a very small amount among the stroma cells in mesenchymal tissue and known to not only differentiate into connective tissue cells such as osteocytes, chondrocytes, and adipocytes, but also have differentiation potency into nerve cells and cardiomyocytes.

Sources of the mesenchymal stem cells include bone marrow, peripheral blood, umbilical cord blood, fetal embryos, and brain, but are preferably mesenchymal stem cells derived from human bone marrow or blood (bone marrow mesenchymal stem cells), in particular, human bone marrow mesenchymal stem cells in the present invention. The bone marrow mesenchymal stem cells have advantages in that 1) marked effects can be expected, 2) risk of side effects is low, 3) sufficient supply of donor cells can be expected, and 4) therapies with them are noninvasive and they can be autografted and therefore 5) risk of infection is low, 6) immunorejection does not need to be worried about, 7) they have no ethical problems, 8) they are likely to be accepted socially, and 9) they are likely to become a therapy widely used as a general medical care. Furthermore, the bone marrow transplantation therapy is a therapy already used on the clinical site and its safety is confirmed. Moreover, stem cells derived from bone marrow are highly migratory and not only by the transplant to the local site but also by intravenous administration, they can be delivered to lesional tissue and the therapeutic effect can be expected there.

The cells may be cells obtained by inducing differentiation of ES cells or induced pluripotent stem cells (iPS cells or the like), an established cell line, or cells isolated from the living body and proliferated. The cells may be derived from allogeneic cells or autologous cells, but they are preferably mesenchymal stem cells derived from autologous cells (derived from patient's own cells).

The mesenchymal stem cells used in the present invention are cells that are negative for CD24, a differentiation marker, and maintained in an undifferentiated state. Therefore, the cells have properties of having high proliferation and survival rates after the introduction into the living body. The inventors have developed a method for obtaining such undifferentiated mesenchymal stem cells, details of which are described in WO2009/002503.

Besides CD24, the mesenchymal stem cells used in the present invention are characterized by being positive for at least one or more selected from CD73, CD90, CD105, and CD200 and/or negative for at least one or more selected from CD19, CD34, CD45, CD74, CD79α, and HLA-DR. Preferably, the mesenchymal stem cells used in the present invention are characterized by being positive for 2 or more of CD73, CD90, CD105, and CD200 and negative for 4 or more of CD19, CD34, CD45, CD74, CD79α, and HLA-DR. More preferably, the mesenchymal stem cells used in the present invention are characterized by being positive for CD73, CD90, CD105, and CD200 and negative for CD19, CD34, CD45, CD74, CD79α, and HLA-DR.

In the aforementioned method developed by the inventors, cells separated from a bone marrow aspirate or the like under conditions in which the cells do not come in substantial contact with an anticoagulant (heparin or the like) are proliferated in a medium containing human serum (preferably autologous serum) and containing no anticoagulant (heparin or the like) or an anticoagulant at a very low concentration. The phrase "containing no anticoagulant or an anticoagulant at a very low concentration" means not containing an amount of anticoagulant effective as an anticoagulant. Specifically, while the amount effective as an anticoagulant is usually about 20 to 40 U/mL, for example, for heparin or a derivative thereof, the method developed by the inventors decreases, by minimizing the amount added beforehand into a blood collection tube for sampling, the amount in a sample harvested from a living body to less than 5 U/mL, preferably less than 2 U/mL, and further preferably less than 0.2 U/mL and the amount present in a medium in which the cells are cultured to less than 0.5 U/mL, preferably less than 0.2 U/mL, and further preferably less than 0.02 U/mL in volume of medium (see WO2009/034708).

The density of the cells in the medium has an effect on properties and the direction of differentiation of the cells. In the case of mesenchymal stem cells, cell densities in a medium higher than 8,500 cells/cm$^2$ change the properties of the cells and therefore it is preferred to passage the cells at a cell density lower than or, at most, equal to 8500/cm$^2$ and it is more preferable to passage the cells at a time point when the cell density become equal to or higher than 5500/cm$^2$.

In the aforementioned method that the inventors developed, a human serum-containing medium is used and therefore, in consideration of the burden on the serum donor, it is desirable that the number of the medium change is as little as possible and, for example, the medium change is conducted at least once a week and more preferably 1 to 2 times a week.

In the culture, the cells are repeatedly passaged until the total number of the cells reaches $10^8$ or more. The number of required cells may vary depending on the purpose of use, but for example, the number of mesenchymal stem cells required for the transplant for treating cerebral infarction is considered to be equal to or higher than $10^7$. According to the method that the inventors developed, $10^7$ mesenchymal stem cells can be obtained in about 12 days.

The proliferated MSCs may be stored by techniques such as the cryopreservation (for example, in a deep freezer at –152 degrees Celsius) until use as needed. In cryopreservation, a medium (a medium for mammalian cells such as RPMI) is used as a cryopreservation medium containing serum (preferably human serum, more preferably autologous serum), dextran, DMSO. For example, cells can be suspended in a cryopreservation medium containing 20.5 mL of RPMI sterilized by usual filtration, 20.5 mL of self-serum collected from a patient, 5 mL of dextran, and 5 mL of DMSO and cryopreserved at –150 degrees Celsius. Examples of DMSO and dextran include, but are not limited to, Cryosery made by Nipro Corporation and Low Molecular Dextran L Injection made by Otsuka Pharmaceutical Co., Ltd., respectively.

[Cell-Based Medicament (Cellular Preparation)]

The higher the number of the MSCs contained in the synapse formation agent and brain plasticity promoter according to the present invention is, the more preferable it is. However, it is practical to be the minimum number at which the MSCs are effective in consideration of the timing at which they are administered to a subject and the time required for the culture. Accordingly, in a preferred aspect of the synapse formation agent and brain plasticity promoter according to the present invention, the number of mesenchymal stem cells is $10^7$ or more, preferably $5 \times 10^7$ or more, more preferably $10^8$ or more, further preferably $5 \times 10^8$ or more. The number of the dose is not limited to once and may be administered 2 or more times.

The synapse formation agent and brain plasticity promoter according to the present invention is preferably a formulation for parenteral administration, more preferably a formulation for parenteral systemic administration, and particularly a formulation for intravenous administration. Examples of the dosage form suitable for the parenteral administration include injections such as solution-type injections, suspension-type injections, emulsion-type injections, and injections prepared at time of use and grafts. The formulation for parenteral administration is in the form of an aqueous or nonaqueous isotonic aseptic solution or suspension and is formulated into an appropriate unit dosage form in combination with, for example, a pharmacologically acceptable carrier or vehicle, such as, specifically, sterile water or physiological saline, a medium (medium particularly used in the culture of mammalian cells, such as RPMI), a physiological buffer solution such as PBS, a vegetable oil, an emulsifier, a suspension, a surfactant, a stabilizer, an excipient, a vehicle, a preservative, a binder, or the like, as appropriate.

Examples of an aqueous solution for injection include physiological saline, a medium, physiological buffer solutions such as PBS, isotonic solutions containing glucose and/or another adjuvant, for example, D-sorbitol, D-mannose, D-mannitol, sodium chloride, or the like, which may be used in combination with a suitable solubilizing agent, for example, alcohol, more specifically; ethanol, polyalcohol, propylene glycol, polyethyleneglycol, and non-ionic surfactants, for example, polysorbate 80, HCO-50, or the like.

The synapse formation agent and brain plasticity promoter according to the present invention are useful in the treatment of dementia, a chronic phase of cerebral infarction, a chronic phase of spinal cord injury, and neurodegenerative diseases because of their synapse formation and plasticity promoting effects in lesions in the hippocampus or the like.

[Treatment of Dementia]

The inventors have demonstrated that the cognitive function is improved by intravenous administration of MSCs and vascular dementia can be treated with MSCs in stroke-prone spontaneously hypertensive rats.

In vascular dementia, the blood-brain barrier is disrupted by high blood pressure and the decline of the cognitive function (dementia) develops by the occurrence of lacunar infarction, cerebral white matter lesions, and microhemorrhage. The disruption of the blood-brain barrier is also observed in Alzheimer-type dementia and deposition of β amyloid is also found in vascular dementia. Meanwhile, the accumulation of β amyloid does not always result in the development of Alzheimer-type dementia. Accordingly, vascular dementia and Alzheimer-type dementia have similarities in pathology and the border between them is not clear. Therefore, the improvement of the cognitive function by MSCs can be expected also in Alzheimer-type dementia.

[Treatment of Chronic-Phase Cerebral Infarction]

Cerebral infarction refers to a pathological condition in which cerebral ischemia occurs due to cerebral artery occlusion or stenosis and brain tissue undergoes necrosis or a similar state. MSCs have the protective effect on the brain (parenchyma and blood vessels) and the intravenous administration of MSCs reduces the ischemic lesion volume and improves the behavioral function in the acute and subacute phases of cerebral infarction.

Necrotized cells and damaged nerve fibers in the chronic phase are not restored to their original states. Therefore, the main objective of treatment in the chronic phase of cerebral infarction has been considered to be the prevention of the recurrence as well as the restoration of survived cells around the necrotized cells and/or dysfunctioned cells to alleviate the pathological conditions. However, the synapse formation agent and brain plasticity promoter according to the present invention make it possible to restore the motor function and the brain functions by promoting the reconstruction of neural circuits and compensation by normal tissue even in the chronic phase of cerebral infarction.

[Treatment of Chronic-Phase Spinal Cord Injury]

The central nervous system including the spinal cord, unlike the peripheral nerves, is not restored or reproduced once injured. Particularly, the treatment for chronic-phase spinal cord injury with advanced scarring is difficult and clinical trials using ES cells have been conducted, but with no success. However, the synapse formation agent and brain plasticity promoter according to the present invention make it possible to restore the motor function and the neural functions by promoting the reconstruction of neural circuits and compensation by normal tissue even in the chronic phase of cerebral infarction.

[Treatment of Neurodegenerative Disease]

The synapse formation agent and brain plasticity promoter according to the present invention are useful for neurodegenerative diseases, such as amyotrophic lateral sclerosis (ALS), Parkinson's disease, progressive supranuclear palsy (PSP), Huntington's disease, multiple system atrophy (MSA), striatonigral degeneration (SND), Shy-Drager syndrome, olivopontocerebellar atrophy (OPCA), and spinocerebellar degeneration (SCD).

[Treatment of Mental Disease]

Besides the diseases mentioned above, the synapse formation agent and brain plasticity promoter according to the present invention are useful for mental diseases such as schizophrenia, manic depression, personality disorder, mood disorder, impaired mental development, stress-related disorder, autism, learning disability, behavior/emotional disorder, mental retardation, sleep disorder, eating disorder, identity disorder, dissociative disorder, adjustment disorder, alcoholic disorder, and dependence.

[Higher Function]

The synapse formation agent and brain plasticity promoter according to the present invention can improve higher functions in attentional dysfunction, memory impairment, aphasia, lapse of memory, apraxia, executive function disorder, emotional disorder, and the like, in addition to the improvement of the motor function and simple cognitive functions.

[Rehabilitation]

The effect of the treatment with the synapse formation agent and brain plasticity promoter according to the present invention is markedly increased by using it in combination with rehabilitation. It is known that rehabilitation improves the plasticity in patients with cerebral infarction or spinal cord injury. However, the combination of the treatment with the synapse formation agent and brain plasticity promoter according to the present invention and rehabilitation synergistically improves their plasticity-promoting functions.

As described above, the synapse formation agent and brain plasticity promoter according to the present invention make it possible to treat dementia, chronic-phase cerebral infarction, chronic-phase spinal cord injury, neurodegenerative diseases, and the like, which have conventionally been considered to be difficult to treat, by the promotion of reconstruction of neural circuits and the plasticity by the synapse formation along with the tissue repair of the damage sites.

EXAMPLES

The present invention will be specifically described by Examples below, but the present invention is not limited by these Examples.

Example 1. Synapse Formation and Promotion of Plasticity in Cerebral Infarction Rat 1. Materials & Methods (1) Preparation of Mesenchymal Stem Cells Derived from Rat Bone Marrow The experiment was carried out in accordance with the institutional guidelines for Animal Experiments in Sapporo Medical University. According to previous reports, the bone marrow obtained from femoral bones of adult SD rats was diluted to 25 ml with Dulbecco's modified Eagle medium (DMEM) supplemented with 10% heat-inactivated FBS, 2 mM l-glutamine, 100 U/ml penicillin, and 0.1 mg/ml streptomycin were added, and the bone marrow was incubated for 3 days at 37 degrees Celsius in 5% $CO_2$ atmosphere (Kim S. et al., Brain Res. 2006, 1123:27-33. Ukai R. et al., J. Neurotrauma. 2007, 24:508-520.). The bone marrow was cultured until confluent and adherent cells were detached with trypsin-EDTA and passaged at a density of $1 \times 10^4$ cells/ml three times to obtain mesenchymal stem cells (MSCs).

(2) Cerebral Infarction Model

As a cerebral infarction model, the rat transient middle cerebral artery occlusion (tMCAO) model was used. According to previous reports, adult female SD rats (200 to 250 g) were anesthetized with ketamine (75 mg/kg) and xylazine (10 mg/kg) and a 20.0 to 22.0 mm of intraluminal suture (MONOSOF) was inserted from an external carotid artery to induce transient middle cerebral artery occlusion (Honma T. et al., Exp. Neurol. 2006; 199: 56-66. Sasaki M. et al., Methods Mol. Biol. 2009; 549: 187-195.).

(3) Immunohistochemistry 1 ml of DMEM containing MSCs ($1.0 \times 10^6$ cells each) labeled with GFP was administered intravenously to rats at 8 weeks after establishing occlusion. Rats were anesthetized with ketamine (75 mg/kg) and xylazine (10 mg/kg) in week 6 after administration of GFP-MSCs and perfused with 200 ml of phosphate-buffered saline (PBS) and 4% PFA. Brain tissue was dissected out. 4% PFA was infiltrated into the brain tissue for 4 hours and then PBS containing 30% sucrose was infiltrated into the tissue for 24 hours. The brain tissue was then immersed in an embedding agent for cryo-sectioning (Tissue-Tek, Torrance, Calif.) and then stored at −80 degrees Celsius until use. Coronal sections were cut to 50-μm thickness, stained with DAPI, then coverslipped with VECTASHIELD (Vector Laboratories, Burlingame, Calif.), and observed using a confocal microscope with Ex/Em (405; 561: LSM780 ELYRA S.1 system).

(4) fMRI (Functional Magnetic Resonance Imaging)

1 ml of DMEM containing MSCs ($1.0 \times 10^6$ cells each) was administered intravenously to rats. Cyclosporine A (10 mg/kg) was administered intraperitoneally every day. The measurement with fMRI was conducted under anesthesia 42 days after the administration of MSCs. The fMRI analysis of change in signal in the right somatic sensory area of the cortex was conducted with T2-weighted images obtained by producing electrical stimulation (1 mA, pulse; 3 times/sec) using Electric Pulse Generator: Master-8 (A. M. P. I.) through an indwelling electrical stimulation needle in the left upper limb of the rats.

(5) DTI (Diffusion Tensor Image) Analysis

The brain was fixed by perfusion 42 days after onset of cerebral infarction and the fixed brain was immersed in 4% PFA for 2 weeks or longer. The fixed brain was transferred into a centrifuge tube after 2 weeks and the test tube was filled with Fluorinert (a fluorine-based inert liquid) to prepare a specimen for MRI imaging.

Animal MRI:
  Spatial resolution; 200 μm×200 μm (number of matrices; 256×256)
  Slice thickness; 350 μm
  FOV (in section); 25.6 mm×25.6 mm, FOV (rostro-caudal direction); 15.4 mm
  Number of slices; 44
  Sequence; Stejskal-Tanner spin-echo diffusion sequence
  Number of diffusion sensitizing gradient directions; 6 directions, vectors; [1, 0, 1], [−1, 0, 1], [0, 1, 1], [0, 1, −1], [1, 1, 0] [1, −1, 0]
  b-value; 809 sec/mm² (8=8.5 msec, Δ=12.5 msec)
  TR/TE; 5000/30 ms
  No. of Averages; 10
  Imaging time; 12 hours 38 minutes 45 seconds
Tractgraphy Analysis:
  Software for analysis: Diffusion Toolkit (tensor image calculation), TrackVis (tract drawing), either of which was downloaded for free from http://trackvis.org
  Method of analysis: Total six ROIs: right and left cortexes, external capsules, and internal capsules were defined as anatomical indexes referring to the b=0 images (T2-weighted images). The neural network was then analyzed by drawing tractography in arbitrary combinations of ROIs in the assumption of 10 patterns of nerve fiber network.

2. Results

Figure 1:
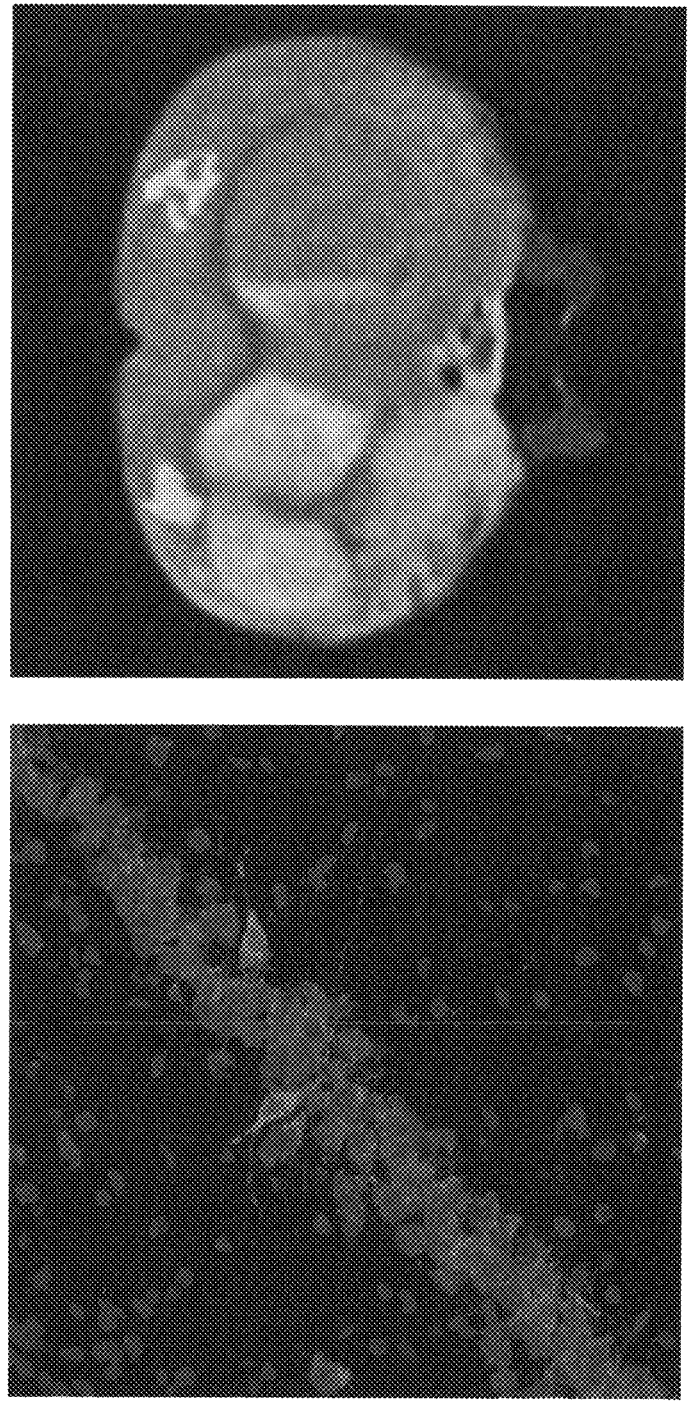
FIG. 1 illustrates the synapse formation (left) and promotion of plasticity (right: fMRI image) in a cerebral infarction model rat given MSCs. Left: administered GFP-MSCs have reached the hippocampus and differentiated into neurons to grow neurites and form synapses. Right: 1 to 2 weeks after the administration of MSCs. White color indicates infarction sites. Motor sensory areas in the infarction region as well as motor sensory areas in the contralesional region are activated.

The DAPI staining image indicated that intravenously administered GFP-MSCs reach the hippocampus and differentiate into neurons to grow neurites and form synapses (FIG. 1, left).

The result of the fMRI analysis indicated that not only motor sensory areas in the infarction region, but also contralesional motor sensory areas are activated by the administration of MSCs (the promotion of plasticity in the infarction site and the contralesional site) (FIG. 1, right). In other words, it was indicated that the administration of the MSCs activates the neural network between the right and left brains, which are usually not used. This suggests that effect of the administration of MSCs may be obtained also in a chronic phase of cerebral infarction and higher brain dysfunction.

Figure 2:
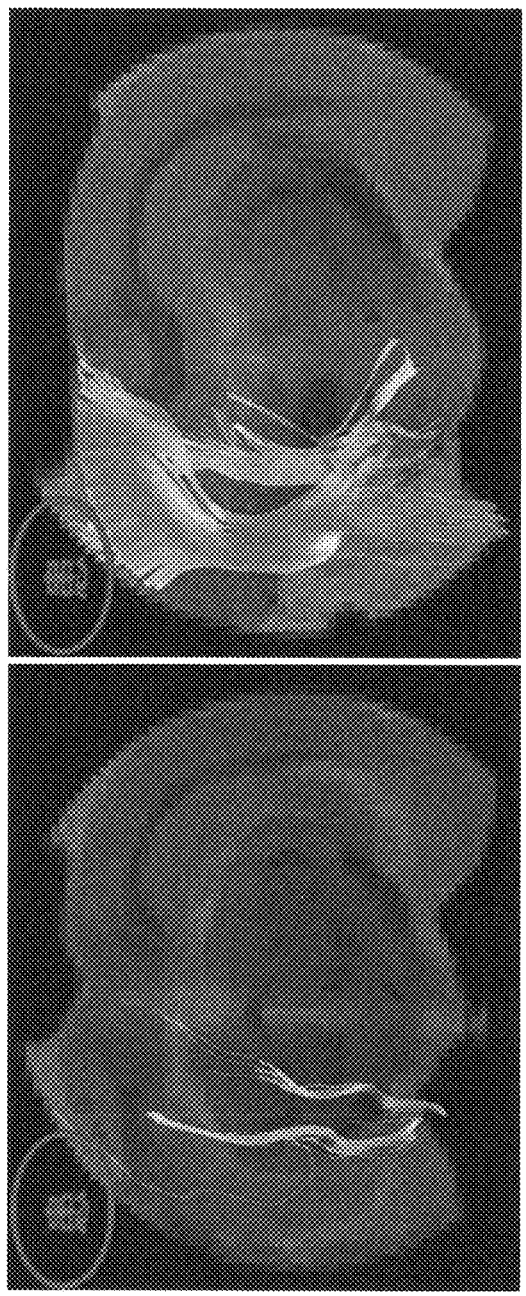
FIG. 2 illustrates DTI in cerebral infarction model rats. In the control, the number of active nerves is decreased by cerebral infarction (left). In the MSC administration group, the plasticity is promoted, compensated regions are not only in the motor sensory areas, but also extended to the surrounding cortexes (beyond the normal range) and the number of motor nerve fibers is also increased (right).
Figure 3:
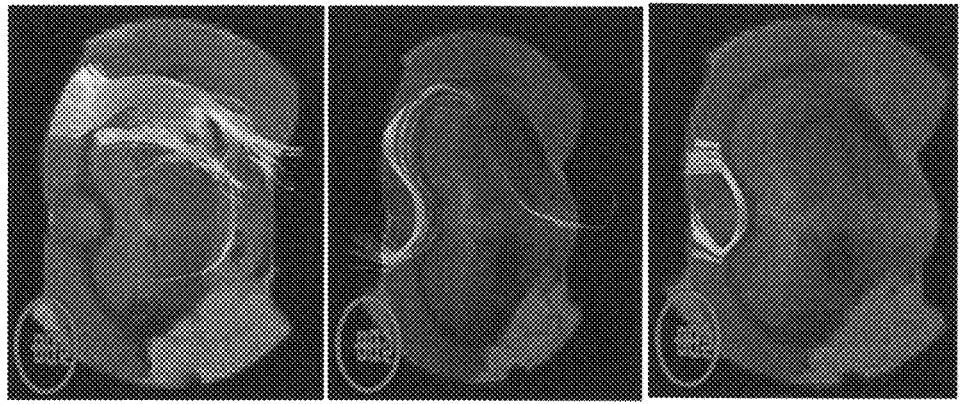
FIG. 3 illustrates DTI in cerebral infarction model rats. (Top) Plasticity on the unaffected side: Cortex ROI on the unaffected side–Internal capsule ROI on the unaffected side; (Middle) Cortex on the affected side→Unaffected side: Cortex ROI on the affected side–External capsule ROI on the unaffected side; (Bottom) Left and right networks: Cortex ROI on the affected side–Cortex ROI on the unaffected side.
Figure 3:
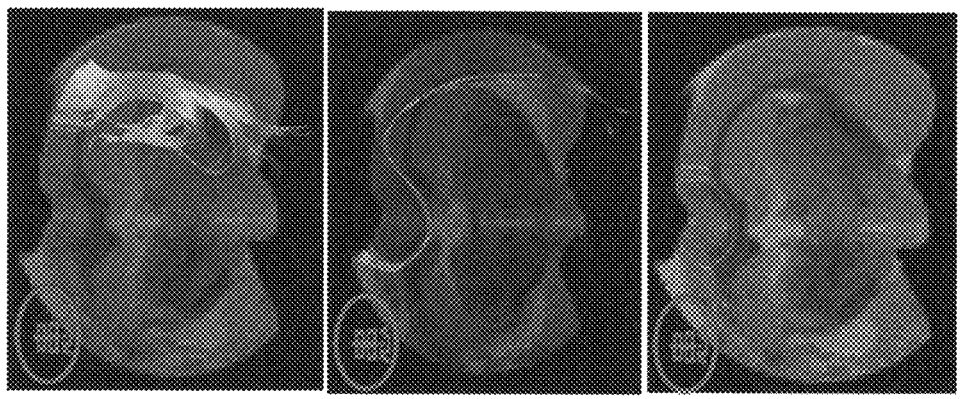

The result of the DTI analysis indicated that while the number of active nerves is decreased by cerebral infarction in the control (vehicle administration) (FIG. 2, left), the plasticity is promoted and compensated regions are not only in the motor sensory area, but also extended to the surrounding cortex (beyond the normal range) and the number of motor nerve fibers is also increased in the MSC administration group (FIG. 2, right). It was also indicated that the brain plasticity on the unaffected side is promoted and the number of motor nerve fibers is increased (FIG. 3, top and middle) and the number of left and right neural networks is also increased (FIG. 3, bottom) in the MSC administration group, in comparison with the control.

These results revealed that the administration of MSCs facilitates not only the reproduction and plasticity in the lesion and surrounding tissue, but also the reproduction and plasticity of the whole central nervous system including the contralesional side of the brain. Therefore, it has become possible to induce not only the restoration of relatively simple functions including the restoration of the motor function, but also the restoration of higher and complex neural functions such as the restoration of higher brain functions (including aphasia).

Example 2. Therapeutic Effect in Vascular Dementia Rat

Stroke-prone spontaneously hypertensive rats (SHRSP) develop dementia by having a disruption of the BBB (blood-brain barrier) due to high blood pressure and generating lacunar infarction or the like. Therefore, the effect of the administration of MSCs on dementia was examined by three methods: MWM (water maze test), NOR (novel object recognition test), and NOP (novel object placement test) in SHRSP rats as a vascular dementia model. NOR and NOP were conducted in week 1 before transplant, and week 1 and week 4 after transplant and MWM was conducted in week 5 after transplant.

1. Materials & Methods (1) Vascular Dementia Model Rat (SHRSP Rat)

The SHRSP rats were purchased from Hoshino Laboratory Animals, Inc. These rats are stroke-prone spontaneously hypertensive rats established by selecting the offspring having a parent who died of stroke every generation and crossbreeding the offspring and vascular dementia model rats that develop dementia by having a disruption of the blood-brain barrier due to high blood pressure and generating lacunar infarction or the like. In this Example, rats having experienced cerebral infarction or cerebral hemorrhage at 16 to 20 weeks were selected as subjects and divided, after pre-treatment evaluation, into two groups: the MSC administration group and the vehicle (DMEM) administration group for the following tests.

(2) Morris Water Maze Test (MWM)

For the MWM, a circular swimming pool having a diameter of 1.3 m was filled to a depth of 30 cm with opaque water at a water temperature of 24 degrees Celsius and a platform to be the goal was placed just under the surface of the water. Rats were put in the swimming pool at the edge of the pool and latency to reach the platform [LRP] was measured.

The measurement was carried out by video tracking (Anymaze tracking software (Stoelting Co.; Wood Dale, Ill., USA)) for consecutive 6 days in week 5 after transplant. 4 cycles of 1 minute device adaptation was conducted on day 1 and LRP was measured for consecutive 5 days from day 2. The measurement was conducted 4 cycles a day and the mean of the measurements was used.

(3) Novel Object Recognition (NOR)

Before the task, device adaptation was conducted for 15 minutes a day for 3 days per subject. NOR was tested on day 4.

NOR was composed of (1) the sample phase, (2) the delay phase, and (3) the test phase. In the sample phase, two identical objects were placed at the positions that are 10 cm from two respective walls, in an open field and the subjects were allowed to explore freely. After the sample phase, the subjects were returned to their home cages. 5 minutes later, the subjects were brought back in the open field again to start the test phase. In the test phase, the object used in the sample phase (Familiar object: Object F) was placed near one wall and a new object (Novel object: Object N) was placed near the other wall. As an action criterion, an object exploration action was defined as an action of a subject that brings its nose within 2 cm from an object.

The evaluation was made based on the value (N/N+F) expressed in % obtained by dividing the exploration time for Object N by the total exploration time for the two objects using the object exploration time in the test phase.

(4) Novel Object Placement (NOP)

NOP was tested on day 5. NOP was composed of three phases like NOR. In the test phase, the same objects as those used in the sample phase were used, but one object was placed at the same position as that in the sample phase (Familiar object: Object F) and the other one was placed at a different position (Novel object: Object N).

Like NOR, the evaluation was made based on the value (N/N+F) expressed in % obtained by dividing the exploration time for Object N by the total exploration time for the two objects using the object exploration time in the test phase.

(5) Evans Blue Staining (Evaluation of Blood-Brain Barrier)

Model rats 1 week after the intervention were anesthetized with ketamine (75 mg/kg) and xylazine (10 mg/kg) and FITC-lectin (1.6 mg/kg, Sigma, Taufkirchen, Germany) and Evans Blue (EvB) (4% EvB in saline, 4 mL/kg, Sigma) were administered to the model rats from the femoral vein.

The rats were sacrificed just after the administration and perfused with 200 ml of phosphate-buffered saline (PBS). The brain tissue was dissected out, shock frozen in isopentane, and stored at −80 degrees until use. In sample preparation, the tissue was sliced into 30 μm coronal sections and post-fixed in 4% PFA. The sites at 1.60 to 6.80 mm posterior to the bregma were observed with LSM780 confocal laser microscope (Laser: Argon 488 for FITC-lectin, 561 for EvB; Objective: Plan-Apochromat 10×/0.45 M27, Zeiss, Jena, Germany).

(6) Blood Vessel Pericyte and Endothelial Cell Counts

Rats were anesthetized with ketamine (75 mg/kg) and xylazine (10 mg/kg) in week 6 after transplant and perfused with 200 ml of phosphate-buffered saline (PBS) and 4% PFA. The brain tissue was dissected out. 4% PFA was infiltrated into the brain tissue for 4 hours and then 15% and 30% sucrose were infiltrated into the tissue for 24 hours. The brain tissue was then immersed in an embedding agent for cryosectioning (Tissue-Tek, Torrance, Calif.), then flash-frozen in isopentane, and stored at −80 degrees.

For sample sections, the tissue was sliced into 30 μm coronal sections. The sites at 1.60 to 6.80 mm posterior to the bregma were observed so as to include the whole hippocampus. The samples were blocked with 10% goat serum for 30 minutes and stored with a primary antibody dissolved in 5% goat serum in a refrigerator at 4 degrees Celsius overnight. The samples were washed with PBS on the next day and then allowed to react with a secondary antibody dissolved in 5% goat serum at room temperature for 2 hours. The antibody used for pericytes was an anti-PDGFRβ antibody and the antibody used for vascular endothelium was an anti-RECA antibody.

The observation was carried out using LSM780 confocal microscope (Laser: Argon 488, 561; Objective: Plan-Apochromat 10×/0.45 M27, Zeiss, Jena, Germany).

For the quantitative measurement, the RECA-positive blood vessel length was measured as the vascular endothelium length and the PDGFRβ-positive blood vessel length was measured as the pericyte-positive blood vessel length. The measurement was performed using Image J. Each length was measured and the pericyte coverage rate was calculated by dividing the pericyte-positive blood vessel length by the vascular endothelium length and expressed in % for evaluation.

(7) MRI T2-Weighted Image (Evaluation of Lateral Ventricle Volume)

Rats were anesthetized with ketamine (75 mg/kg) and xylazine (10 mg/kg) and the head was fixed in a coil and photographed. To monitor the change over time in lateral ventricle volume, MRI measurements were performed before intervention, and in week 1, week 3, and week 4 after intervention. The MRI measurements were performed using a 7-Teslar, 18-cm-bore superconducting magnet (Oxford Magnet Technologies) interfaced to a UNITYINOVA console (Oxford Instruments) as described previously (Honma T. et al., Exp. Neurol. 2006, 199:56-66., Komatsu K. et al., Brain Res. 2010, 1334:84-92.).

T2-weighted images were obtained. The lateral ventricle volumes were measured using image processing software (Scion Image, Version Beta 4.0.2, Scion Corporation) from serial images obtained from the T2-weighted images (Neumann-Haefelin et al., 2000).

(8) Thickness of Cerebral Cortex and Corpus Callosum

To investigate the thickness of cerebral cortex and corpus callosum, measurements were conducted using Nissl-stained samples. Rats were anesthetized with ketamine (75 mg/kg) and xylazine (10 mg/kg) in week 6 after transplant and perfused with 200 ml of phosphate-buffered saline (PBS) and 4% PFA. The brain tissue was dissected out.

4% PFA was infiltrated into the brain tissue for 4 hours and 15% and 30% sucrose were then infiltrated for 24 hours. The brain tissue was then immersed in an embedding agent for cryosectioning (Tissue-Tek, Torrance, Calif.), then flash-frozen in isopentane, and stored at −80 degrees.

The samples were cut into 30 μm coronal sections and subjected to Nissl staining. The thicknesses of cerebral cortex and corpus callosum in the M1 to S1 region were measured at three places each in a slice 3.3 mm posterior to the bregma using the polarizing microscope Olympus BX51 (4× objective) and Stereo Investigator software (MicroBrightField) and the means were expressed as the measurements.

(9) Nerve Cell Counts in Hippocampus

To investigate the nerve cell counts in the hippocampus, the measurement was conducted using Nissl-stained samples. Rats were anesthetized with ketamine (75 mg/kg) and xylazine (10 mg/kg) in week 6 after transplant and perfused with 200 ml of phosphate-buffered saline (PBS) and 4% PFA. The brain tissue was dissected out.

4% PFA was infiltrated into the brain tissue for 4 hours and 15% and 30% sucrose were then infiltrated for 24 hours. The brain tissue was then immersed in an embedding agent for cryosectioning (Tissue-Tek, Torrance, Calif.), then flash-frozen in isopentane, and stored at −80 degrees Celsius.

The samples were cut into 30 μm coronal sections and subjected to Nissl staining. Nerve cell counts in the whole hippocampus were determined using the polarizing microscope Olympus BX51 and StereoInvestigator software (MicroBrightField).

2. Results

Figure 4:
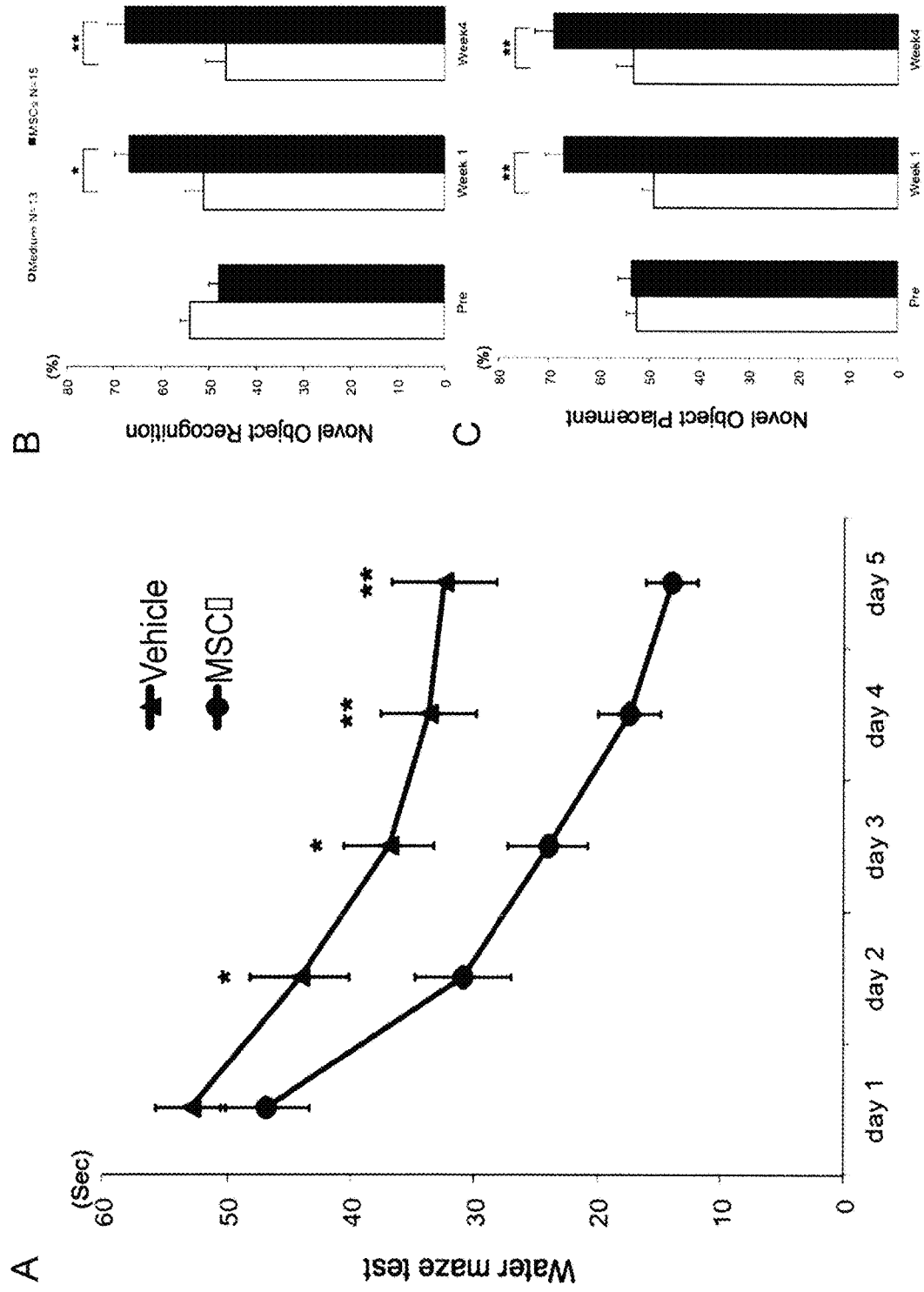
FIG. 4 illustrates the effect of MSCs in vascular dementia model rats.

All the three tests for cognitive function indicated that the administration of MSCs improves the cognitive function of the model mouse (FIG. 4).

The result of Evans Blue staining indicated that Evans Blue (red), which should remain in the blood vessels in the normal brain, is leaked out to the outer tissue from the blood vessels and the blood-brain barrier is broken in the control (vehicle) group (FIG. 5, left), but improvement is found in the MSC administration group (FIG. 5, right).

The blood-brain barrier is composed of endothelial cells, pericytes, and astrocytes. The result of the immunostaining indicated that the administration of MSCs increases the number and the length of endothelial cells and pericytes in the blood-brain barrier (FIG. 6). Particularly, the improvement in coverage of endothelial cells, which are important for maintaining the function of the blood-brain barrier, by pericytes (pericyte coverage rate) was indicated.

The result of lateral ventricle volume measurement with the T2-weighted images indicated that the atrophy of brain, which means progression of dementia, is advanced in the control (vehicle) group (FIG. 7A: particularly the lower left corner of the vehicle image: white color indicates water; enlargement of cerebral ventricle is visible). In contrast, the atrophy of the brain is dramatically ameliorated in the MSC administration group in comparison with the control group (FIG. 7A: the lower left corner of the MSC image). The effect of the administration of MSCs is clearer when quantified (FIG. 7B).

Moreover, it was also indicated that the thickness of cerebral cortex and corpus callosum is improved in the MSC administration group (FIG. 8) and that the cell count in the hippocampus is also improved (FIG. 9).

As described in the foregoing, high therapeutic effect was found since the administration of MSCs provides treatment against the cause of dementia and treatment for regeneration of cerebral neurons simultaneously.

Example 3. Therapeutic Effect on Patients with Chronic-Phase Cerebral Infarction MSCs were intravenously administered to patients with chronic-phase cerebral infarction and the improvement of the higher function level was evaluated.

1. Method

Bone marrow aspirates were harvested from the ilium of patients with cerebral infarction under local anesthesia. Cells of interest were separated from the bone marrow aspirates in the Cell Processing Center (CPC) and cultured to obtain about 10000 times of cells in about 2 weeks. About $1 \times 10^8$ cells were enclosed in a bag with a capacity of about 40 ml under the GMP management to produce a cellular preparation. This cellular preparation was transplanted by intravenous administration for 30 minutes to 1 hour.

A placebo was administered for 150 days in the first half (Clinical trial I). MSCs were administered on day 150. Higher functions were evaluated until day 250 (Clinical trial II).

(1) Aphasia Quotient

The WAB aphasia test was performed on day 40 after onset (the time of changing hospital), day 76 after onset, day 141 after onset (before administration of cells), day 187 after onset (34 days after administration of cells), and day 250 after onset (97 days after administration of cells). This test include 38 test items under the eight main items: spontaneous speech, auditory comprehension, repetition, naming, reading, writing, praxis, and construction and allows the classification of aphasia as well as the calculation of aphasia quotient, which represents the severity of aphasia.

(2) Processing Speed

The WAIS-III test was performed on day 40 after onset (the time of transfer to another hospital), day 141 after onset (before administration of cells), and day 250 after onset (97 days after administration of cells) and the processing speed was calculated.

(3) Motor Function

The motor function of patients was evaluated using mRS and the FUGL MEYER score. MSCs were administered after day 150 (chronic phase, Clinical trial II), 2. Results In the first half (Clinical trial I), the scores were maintained stably at low levels due to the placebo administration. However, the shift to Clinical trial II after day 150 and the start of the administration of MSCs resulted in marked improvement in both of aphasia quotient and processing speed (FIG. 10A, Table 1).

TABLE 1

| | Day 40 after onset Time of changing hospital | Day 76 after onset | Day 141 after onset Before administration of MSCs | Day 187 after onset Day 34 after administration | Day 250 after onset Day 97 after administration |
|---|---|---|---|---|---|
| Aphasia quotient (WAB) | 14 | 21.5 | 23.2 | 24.2 | 35.5 |

TABLE 1-continued

| | Day 40 after onset Time of changing hospital | Day 76 after onset | Day 141 after onset Before administration of MSCs | Day 187 after onset Day 34 after administration | Day 250 after onset Day 97 after administration |
|---|---|---|---|---|---|
| Processing speed (WAIS) | 66 | — | 66 | — | 75 |

All patients had improvement by one or more mRS grades (primary endpoint) and 75% of patients had improvement by two mRS grades (secondary endpoint) (FIG. 10B), indicating that marked improvement in function is found by the administration of MSCs (FIG. 10C).

The FUGL MEYER scores were maintained stably at low levels due to the placebo administration in the first half (Clinical trial I), but the administration of MSCs markedly improved the function in the latter half (Clinical trial II). As seen above, the motor function was also markedly improved (FIG. 10D).

Example 4. Combinational Effect with Rehabilitation

1. Materials & Methods
(1) Preparation of Mesenchymal Stem Cells Derived from Rat Bone Marrow According to the description in Example 1, the bone marrow obtained from femoral bones of adult SD rats was diluted to 25 ml with Dulbecco's modified Eagle medium (DMEM) and heat-inactivated 10% FBS, 2 mM 1-glutamine, 100 U/ml penicillin, and 0.1 mg/ml streptomycin were added. The bone marrow was incubated for 3 days at 37 degrees Celsius in 5% $CO_2$ atmosphere (id.). The bone marrow was cultured until confluent and adherent cells were detached with trypsin-EDTA and passaged at a density of $1 \times 10^4$ cells/ml three times to obtain mesenchymal stem cells (MSCs).

(2) Cerebral Infarction Model

As a cerebral infarction model, the rat transient middle cerebral artery occlusion (tMCAO) model was used. According to previous reports, adult female SD rats (200 to 250 g) were anesthetized with ketamine (75 mg/kg) and xylazine (10 mg/kg) and a 20.0 to 22.0 mm of intraluminal suture (MONOSOF) was inserted from an external carotid artery to induce transient middle cerebral artery occlusion (id.).

Sixty minutes after establishing transient middle cerebral artery occlusion, DWI-MRIs were obtained to evaluate the initial stroke volume. Animals with an initial stroke volume less than a standard (300+/−60 $mm^3$) were excluded from the experiment and the rats were randomized into the four groups as follows.
Group 1 (medium; n=10)
Group 2 (medium+exercise (rehabilitation); n=10)
Group 3 (MSC; n=10)
Group 4 (MSC+exercise; n=10)

Cyclosporin A (10 mg/kg) was administered intraperitoneally to all rats every day. The intravenous administration was all from the left femoral vein.

(3) Rehabilitation

After cerebral infarction induction, the rats were forced to run on a treadmill every day for 20 minutes. The exercise was started 1 day after arterial obstruction, at a speed of 3 m/min with a slope of 0 degrees during the first one week, and the speed was increased by 3 m/min every week until the subsequent histologic evaluation.

(4) MRI and Measurement of Ischemic Lesion Volume

Rats were anesthetized with ketamine (75 mg/kg) and xylazine (10 mg/kg) and MRI measurements were performed. The MRI measurements were performed using a 7-Teslar, 18-cm-bore superconducting magnet (Oxford Magnet Technologies) interfaced to a UNITYINOVA console (Oxford Instruments) as described previously (id.).

T2WI-MRI measurements were performed 1, 14, and 35 days after occlusion. The ischemia lesion area was calculated from the MRI image using Scion Image, Version Beta 4.0.2 (Scion Corporation). Lesion volume ($mm^3$) was determined by analysis of high intensity areas on serial images collected through the cerebrum. For each slice, the higher intensity lesions in T2WI-MRI, where the signal intensity was 1.25 times higher than the counterpart in the contralateral brain lesion, were marked as the ischemic lesion area, and infarct volume was calculated taking slice thickness (1 mm) into account. The presence of intracerebral hemorrhage was counted when there is a low intensity area in the T2WI section. Animals with an initial stroke volume less than the standard were excluded from the experiment.

(5) Measurement of Synapse Density (Nerve Cell Count)

To investigate the nerve cell count, the nerve cell count (synapse density) was measured using Nissl-stained samples according to the description in (9) in Example 2.

(6) Measurement of Thickness of Corpus Callosum

To investigate thickness of corpus callosum, the measurement was conducted using Nissl-stained samples according to the description in (8) in Example 2.

(7) Motor Behavior Index (Limb Placement Test)

The limb function was evaluated by the following six items for rats.

Evaluation was made with rats held for tests 1 to 4 and the rats placed on a stand for tests 5 and 6.

Forefeet were evaluated for all the six items and hind legs were evaluated for two items of tests 4 and 6.

For each item, evaluation was made into 4 grades ranging from 0 for no limb placing to 2 for complete limb placing.

(1 is for delayed or incomplete limb placing).

The minimum total score is 0 and the maximum total score is 16.

[Test 1, Forelimbs]

A rat is slowly brought closer toward a table with the rat being about to get on the table. At 10 cm above the table, normal rats stretch and place both forelimbs on the table.

[Test 2, Forelimbs]

With the rat's forelimbs touching the table edge, the head of the rat is moved 45 degrees upward while the chin is supported to prevent the nose and vibrissae from touching the table. A stroke rat may lose contact with the table with the forelimb contralateral to the injured hemisphere.

[Test 3, Forepaws]

Forepaw placement of the rat when facing a table edge is observed. A normal rat places both forelimbs on the table top.

[Test 4, Forelimbs and Hindlimbs]

Forelimb and hindlimb placement when the lateral side of the rat's body is moved toward the table edge is observed.

[Test 5, Forelimbs]

The rat is placed on the table and gently pushed from behind the table edge. A normal rat will grip on the table edge, but an injured rat may drop the forelimb contralateral to the injured hemisphere from the table.

[Test 6, Forelimbs and Hindlimbs]

The rat is placed on the table and gently pushed laterally toward the table edge toward the forelimb contralateral to the injured hemisphere.

(8) Histological Evaluation

Rats were anesthetized with ketamine (75 mg/kg) and xylazine (10 mg/kg) in week 6 after transplant and perfused with 200 ml of phosphate-buffered saline (PBS) and 4% PFA. The brain tissue was dissected out. 4% PFA was infiltrated into the brain tissue for 4 hours and then 15% and 30% sucrose were infiltrated into the tissue for 24 hours. The brain tissue was then immersed in an embedding agent for cryosectioning (Tissue-Tek, Torrance, Calif.), then flash-frozen in isopentane, and stored at −80 degrees. Cortex and striatum samples were cut out from the brain tissue and the expression levels of synaptophysin and PSD-95 were measured using an anti-synaptophysin antibody and an anti-PSD-95 antibody.

2. Results

The results of the MRI measurements indicated that the administration of MSCs only or the combination of the administration of MSCs and rehabilitation reduces high intensity areas (FIG. 11). It was also indicated that the administration of MSCs only or the combination of the administration of MSCs and rehabilitation increases the number (density) of synapses (FIG. 12) and also the thickness of corpus callosum (FIG. 13).

It was also indicated that the administration of MSCs only or the combination of the administration of MSCs and rehabilitation significantly increases the motor behavior index (sensomobility) (FIG. 14). Furthermore, it was also indicated that there are positive correlations between the motor behavior index and the density of the synapse and between the motor behavior index and the thickness of corpus callosum (FIG. 15).

The result of the histological evaluation indicated that the effect of increasing pre-synapses (left) and post-synapses (right) is also found in the cortex on the unaffected side, which has no infarction (FIG. 16). Moreover, it was indicated that the effect of increasing pre-synapses (left) and post-synapses (right) is also found in the striatum on the unaffected side (FIG. 17).

3. Discussion

The foregoing results indicated that the combination of the administration of MSCs and rehabilitation, but not only the administration of MSCs, synergistically improves the brain plasticity.

Example 5. Therapeutic Effect on Chronic-Phase Spinal Cord Injury Model

1. Materials & Methods (1) Rat Chronic-Phase Spinal Cord Injury Model

As a chronic-phase spinal cord injury model, a spinal cord injury model was performed according to previous reports (Matsushita et al., 2015). Adult male SD rats (250 to 300 g) were anesthetized with ketamine (90 mg/kg) and xylazine (4 mg/kg), a laminectomy performed at the T9-10 level spinal cord, and a contusion delivered using the apparatus for generating spinal cord injury (Infinite Horizon Impactor, 60-kilodyne).

(2) Distribution of GFP-MSCs

Rats at 10 weeks after establishing spinal cord injury were received intravenous infusion of MSCs ($1.0 \times 10^6$ cells each) labeled with GFP in 1 ml of DMEM. The rats were anesthetized with ketamine (75 mg/kg) and xylazine (10 mg/kg) after infusion of GFP-MSCs and perfused with 200 ml of phosphate-buffered saline (PBS) and 4% PFA. The spinal cord was dissected out and stained with DAPI, then cover-slipped with VECTASHIELD (Vector Laboratories, Burlingame, Calif.), and observed using a confocal microscope with Ex/Em (405; 561: LSM780 ELYRA S.1 system).

(3) Evaluation of BSCB (Blood Spinal Cord Barrier)

Rats at 10 weeks after establishing spinal cord injury were received intravenous infusion of MSCs ($1.0 \times 10^6$ cells each) in 1 ml of DMEM. Evans Blue was administered to the rats from the thighbone blood vessel 1 week after transplant. The rats were anesthetized with ketamine (75 mg/kg) and xylazine (10 mg/kg) 6 hours later and perfused with 200 ml of phosphate-buffered saline (PBS) and 4% PFA. The spinal cord was dissected out. The spinal cord sample was observed under a microscope and the state of the BSCB (blood spinal cord barrier) was evaluated.

(4) Histological Evaluation

The spinal cord samples 20 weeks after spinal cord injury were blocked with 10% goat serum for 30 minutes and stored with a primary antibody dissolved in 5% goat serum in a refrigerator at 4 degrees Celsius overnight. The samples were washed with PBS on the next day and then allowed to react with a secondary antibody dissolved in 5% goat serum at room temperature for 2 hours. The antibody used for pericytes was an anti-PDGFRβ antibody and the antibody used for vascular endothelium was an anti-RECA antibody.

The observation was carried out using LSM780 confocal microscope (Laser: Argon 488, 561; Objective: Plan-Apochromat 10×/0.45 M27, Zeiss, Jena, Germany).

For the quantitative measurement, the RECA-positive blood vessel length was measured as the vascular endothelium length and the PDGFRβ-positive blood vessel length was measured as the pericyte-positive blood vessel length. The measurement was performed using Image J. Each length was measured and the pericyte coverage rate was calculated by dividing the pericyte-positive blood vessel length by the vascular endothelium length and expressed in % for evaluation.

(5) DTI (Diffusion Tensor Image) Analysis

The rats were perfused and fixed 20 weeks after spinal cord injury and immersed in 4% PFA for 2 weeks or longer. Two weeks later, the fixed spinal cord was transferred into a centrifuge tube and the test tube was filled with Fluorinert (a fluorine-based inert liquid) to prepare a specimen for MRI imaging.

The MRI measurements were performed using a 7-Teslar, 18-cm-bore superconducting magnet (Oxford Magnet Technologies) interfaced to a UNITYINOVA console (Oxford Instruments) as described previously (id.).

2. Results

The behavioral assessment indicated marked improvement in the rats that received the administration of MSCs in comparison with the control (FIG. 18). It was indicated that about 8.6% of the administered MSCs were localized in the damage sites (FIG. 19).

The evaluation using Evans Blue indicated that the permeability of the BSCB is decreased in the MSC administration group (FIG. 20A).

The analysis using an anti-PDGFRβ antibody and an anti-RECA antibody indicated the increase in the number of vascular endothelial cells and the number and the length of pericytes by the administration of MSCs. Furthermore, marked restoration of the BSCB was observed at the cellular level since the coverage of vascular endothelial cells by pericytes is increased (FIG. 20B).

The immunological analysis using an anti-P0 antibody and the analysis with an electron microscope indicated the presence of remyelinated axons, by the administration of MSCs, having a peripheral nerve type of myelin sheath (Schwann cells) characterized by a large nucleus and the basement membrane. Moreover, the result of staining the spinal cord injury lesion with toluidine blue and evaluating the number of remyelinated axons indicated a significantly larger number of remyelinated axons in the MSC group than in the Vehicle group. Therefore, it was indicated that the transplant of MSCs caused remyelination (FIG. 21).

The result of immunostaining of the corticospinal tract (pyramidal tract) in the posterior column of the spinal cord with rabbit anti-protein kinase C-γ (PKC-γ) indicated more regeneration of axons in the MSC group than in the Vehicle group (FIG. 22A). Moreover, the result of 5-HT immunostaining of serotonin fibers (extrapyramidal tract) in the spinal cord anterior horn similarly indicated more regeneration of axons in the MSC group than in the Vehicle group (FIG. 22B). Therefore, it is considered that the administration of MSCs caused axonal regeneration and sprouting in the pyramidal and extrapyramidal tracts.

The result of analysis of the nerve fiber bundle using DTI (FIG. 23) indicated that while the number of spinal nerve fiber bundles is decreased in damage sites, the value was significantly higher in the MSC group than in the Vehicle group. Accordingly, it was indicated that the administration of MSCs increases spinal nerve fibers.

These results revealed that therapeutic effect is shown by various mechanisms also in the chronic phase of spinal cord injury.

Example 6. Therapeutic Effect on Chronic-Phase Cerebral Infarction Model

1. Materials & Methods

Permanent middle cerebral artery occlusion (MCAO) was introduced using a nylon thread to 9-week SD rats. Only the individuals having a cerebral infarction volume of 200 mm$^3$ or more were received transplant in the chronic phase 8 weeks after MCAO.

MSC group: DMEM containing 1.0×10$^6$ MSCs P2 from an SD rat 8 weeks after MCAO in 1 ml was administered from the femoral vein.

DMEM group: 1 ml of DMEM was administered from the femoral vein.

The rats underwent rehabilitation from the next day of the administration and cyclosporine (10 mg/kg) was administered every day for 1 week after the transplant and on alternate days after that. All rats underwent rehabilitation (treadmill with an angle of 0 degrees, a speed of 8 to 12 m/min, 20 minutes) every day from the next day of the transplant. The evaluation of motor function was performed with a treadmill (an angle of 20 degrees) every week.

2. Results

As illustrated in FIG. 24, improvement of motor function was found in the MSC group, but no change was found in the DMEM group. This indicated that the administration of MSCs in the chronic phase of cerebral infarction improves the motor function. This is considered to be because the administration of MSCs facilitated the regeneration and the plasticity.

INDUSTRIAL AVAILABILITY

The present invention makes it possible to rebuild neural circuits and promote the brain plasticity by the formation of synapses and is available in treating dementia, chronic-phase cerebral infarction, chronic-phase spinal cord injury, mental diseases, and the like, which have conventionally been considered to be difficult to treat.

All publications, patents, and patent applications cited herein are incorporated herein by reference as they are.

The invention claimed is:

1. A method for promoting brain plasticity to treat a patient suffering from a chronic phase of cerebral infarction, comprising administering to the patient CD24-negative mesenchymal stem cells derived from human bone marrow or blood wherein the chronic phase of cerebral infarction occurs at least 150 days following an acute cerebral infarction, wherein promoting brain plasticity comprises promoting reconstruction of neuronal circuits and compensation by normal brain tissue in the patient, thereby treating the chronic phase of cerebral infarction.

2. The method according to claim 1, wherein the cells are positive for at least one or more selected from CD73, CD90, CD105, and CD200 and/or negative for at least one or more selected from CD19, CD34, CD45, CD74, CD79a, and HLA-DR.

3. The method according to claim 1, wherein the human bone marrow or blood is bone marrow or blood of a patient receiving administration of the cells.

4. The method according to claim 1, wherein the cells have been proliferated and enriched in a medium containing human serum.

5. The method according to claim 4, wherein the human serum is autologous serum of the patient.

6. The method according to claim 4, wherein the medium comprises a heparin, a heparin derivative, or a salt thereof.

7. The method according to claim 1, wherein the cells are administered via intravenous administration, lumber puncture administration, intracerebral administration, intracerebroventricular administration, local administration, or intraarterial administration.

8. The method according to claim 1, wherein the cells have been proliferated and enriched in a medium containing no anticoagulant or an anticoagulant at less than 0.02 U/mL.

9. The method according to claim 1, wherein higher function of the patient is improved by promoting synapse formation.

10. The method according to claim 1, wherein the patient is suffering from a chronic phase of cerebral infarction, and wherein administration of the MSCs increases the number of synapses.

11. The method according to claim 1, wherein the administration of cells is combined with physical rehabilitation.

* * * * *